United States Patent [19]
Grandy et al.

[11] Patent Number: 5,516,683
[45] Date of Patent: * May 14, 1996

[54] HUMAN D4 DOPAMINE RECEPTOR AND ITS USES

[75] Inventors: David K. Grandy; James R. Bunzow, both of Portland, Oreg.; Olivier Civelli, Aesch, Switzerland; Hubert H.-M. Van Tol, Toronto, Canada

[73] Assignee: State of Oregon, Acting by and Through the Oregon State Board of Higher Education on Behalf of the Oregon Health Sciences University a non-profit organization, Portland, Oreg.

[*] Notice: The portion of the term of this patent subsequent to Aug. 10, 2012, has been disclaimed.

[21] Appl. No.: 56,051

[22] Filed: Apr. 29, 1993

Related U.S. Application Data

[63] Continuation-in-part of Ser. No. 928,611, Aug. 10, 1992, which is a continuation-in-part of Ser. No. 626,618, Dec. 7, 1990, Pat. No. 5,422,265.

[51] Int. Cl.$^6$ .......................... C07K 14/705; C12N 15/12
[52] U.S. Cl. .................. 135/252.3; 435/69.1; 435/320.1; 530/350; 536/23.5
[58] Field of Search ............................... 435/69.1, 252.3, 435/320.1, 7.1; 530/350; 536/23.5

[56] References Cited

PUBLICATIONS

FEBS Let. 243:371–6, Jan. 1989, Deckmann et al Monoclonal Antibodies against the $S_2$–serotonin receptor from rat brain that cross–react with . . . .

Ackenheil et al., 1976, "Antipsychotische wirksamkeit im verhaltnis zum plasmaspiegel von clozapin", Arzneim–Forsch 26: 1156–1158 teach the relationships between the administered dosage, plasma levels and psychological effects of clozapine in schizophrenics.

Cooper et al., 1978, "Catecholamines II: CNS aspects", *The Biochemical Basis of Neuropharmacology*, 3d ed., Oxford University Press, New York, pp. 161–195.

Kebabian & Calne, 1979, "Multiple receptors for dopamine", Nature 277: 93–96.

Botstein et al., 1980, "Construction of a genetic linkage map in man using restriction fragment length polymorphisms", Am. J. Hum. Genet. 32: 314–331.

Amlaiky & Caron, 1985, "Photoaffinity labeling of the $D_2$–dopamine receptor using a novel high affinity radioiodinated probe", J. Biol. Chem. 260: 1983–1986.

Amlaiky & Caron, 1986, "Identification of the $D_2$–dopamine receptor binding subunit in several mammalian tissues and species by photoaffinity labeling", J. Neurochem. 47: 196–204.

Senogles et al., 1986, "Affinity chromatography of the anterior pituitary $D_2$–dopamine receptor", Biochemistry 25: 749–753.

Amlaiky et al., 1987, "Identification of the binding subunit of the $D_1$–dopamine receptor by photoaffinity crosslinking", Mol. Pharmacol. 31: 129–134.

Seeman et al., 1987, "Human brain $D_1$ and $D_2$ dopamine receptors in schizophrenia, Alzheimer's, Parkinson's, and Huntington's diseases", Neuropsychopharm. 1: 5–15.

Seeman, 1987, "Dopamine receptors and the dopamine hypothesis of schizophrenia", Synapse 1: 152–333.

Jarvie et al., 1988, "Dopamine $D_2$ receptor binding subunits of $M_r \approx 140,000$ and 94,000 in brain: deglycosylation yields a common unit of $\approx 44,000$", Mol. Pharmacol. 34: 91–97.

Niznik et al., 1988, "Photoaffinity labeling of dopamine $D_1$ receptors", Biochemistry 27: 7594–7599.

Sengoles et al., 1988, "Purification and characterization of the $D_2$–dopamine receptor from bovine anterior pituitary", J. Biol. Chem. 263: 18996–19002.

Gingrich et al., 1988, "Affinity chromatography of the $D_1$ dopamine receptor from rat Corpus striatum", Biochemistry 27: 3907–3912.

Bunzow et al., 1988, "C,loning and expression of a rat $D_2$ dopamine receptor cDNA", Nature 336: 783–787.

Grandy et al., 1989, "Cloning of the cDNA and gene for a human $D_2$ dopamine receptor", Proc. Natl. Acad. Sci. USA 86: 9762–9766.

Dal Toso et al., 1989, "The dopamine $D_2$ receptor: two molecular forms generated by alternative splicing", EMBO J. 8: 4025–4034.

Casey, 1989, "Clozapine: neuroleptic–induced EPS and tardive dyskinesia", Psychopharmacology 99: 547–553.

Zhou et al., 1990, "Cloning and expression of human and rat $D_1$ dopamine receptors", Nature 346: 76–80.

Sunahara et al., 1990, "Human dopamine $D_1$ receptor encoded by an intronless gene on chromosome 5", Nature 346: 80–83.

Sokoloff et al., 1990, "Molecular cloning and characterization of a novel dopamine receptor ($D_3$) as a target for neuroleptics", Nature 347: 146–151.

Kane et al., 1990, "Clozapine for the treatment–resistant schizophrenic: a double–blind comparison with chlorpromazine", Arch. Gen. Psychiatry 45: 789–796.

Sandoz Canada, Inc., 1990, Clozaril: Summary of preclinical and clinical data.

(List continued on next page.)

*Primary Examiner*—Stephen G. Walsh
*Assistant Examiner*—John D. Uim
*Attorney, Agent, or Firm*—Banner & Allegretti, Ltd.

[57] ABSTRACT

The present invention is directed toward the isolation, characterization and pharmacological use of the human D4 dopamine receptor. The nucleotide sequence of the gene corresponding to this receptor and alleleic variants thereof are provided by the invention. The invention particularly provides recombinant eukaryotic expression constructs capable of expressing the human D4 dopamine receptor at useful levels in cultures of transformed eukaryotic cells. The invention provides cultures of transformed eukaryotic cells which synthesize such useful amounts of human D4 dopamine receptor protein, and methods for characterizing novel psychotropic compounds using such cultures.

10 Claims, 20 Drawing Sheets

PUBLICATIONS

Van Tol et al., 1991, "Cloning of the gene for a human dopamine $D_4$ receptor with a high affinity for the antipsychotic clozapine", Nature 350: 610–614.

Sunahara et al., 1991, "Cloning of the gene for a human dopamine $D_5$ receptor with higher affinity for dopamine than $D_1$", Nature 350: 614–619.

Van Tol et al., 1992, "Multiple domain D4 receptor variants in the human population", Nature 358: 148–152.

Fishburn et al., 1993, "A novel short isoform of the $D_3$ dopamine receptor generated by alternative splicing in the third cytoplasmic loop", J. Biol. Chem. 268: 5872–5878.

Boundy et al., 1993, "Expression and characterization of the rat D3 dopamine receptor: Pharamacologic properties and development of antibodies", J. Pharmacol. Exper. Therap. 264: 1002–1011.

FIG. 1A

```
CGGGGGCGGG ACCAGGGTCC GGCCGGGGCG TGCCCCCGGG GAGGGACTCC CCGGCTTGCC           60

CCCCGGCGTT CTCCGCGGTG CTCAGCGCCC GCCCGGGCGC GCC ATG GGG AAC CGC          115
                                                 Met Gly Asn Arg
                                                  1

AGC ACC GCG GAC GCG GGG CTG CTG GCT GGG CGC GGG CGC GCC GCG              163
Ser Thr Ala Asp Ala Gly Leu Leu Ala Gly Arg Gly Arg Ala Ala
 5                   10                  15                  20

GGG GCA TCT GCG GGG CCA TCT GCG GGG CTC GCT GGG CAG GGC GCG GCG          211
Gly Ala Ser Ala Gly Pro Ser Ala Gly Leu Ala Gly Gln Gly Ala Ala
                25                  30                  35

GCG CTG GTG GGG GGC GTG CTG CTC ATC GGC GCG GTG CTC GCG GGG AAC          259
Ala Leu Val Gly Gly Val Leu Leu Ile Gly Ala Val Leu Ala Gly Asn
            40                  45                  50

TCG CTC GTG TGC GTG AGC GTG GCC ACC GAG CGC GCC CTG CAG ACG CCC          307
Ser Leu Val Cys Val Ser Val Ala Thr Glu Arg Ala Leu Gln Thr Pro
        55                  60                  65

ACC AAC TCC TTC ATC GTG AGC CTG GCG GCC GCC GCC GAC CTC CTC GCT          355
Thr Asn Ser Phe Ile Val Ser Leu Ala Ala Ala Asp Leu Leu Ala
    70                  75                  80
```

FIG. 1B

```
CTC CTG GTG CTG CCG CTC TTC GTC TAC TCC GAG GTC CAG GGT GGC GCG      403
Leu Leu Val Leu Pro Leu Phe Val Tyr Ser Glu Val Gln Gly Gly Ala
 85              90              95             100

TGG CTG CTG AGC CCC CGC CTG GAC GCC CTC ATG GCC ATG GAC GTC          451
Trp Leu Leu Ser Pro Arg Leu Asp Ala Leu Met Ala Met Asp Val
            105             110             115

ATG CTG TGC ACC GCC TCC ATC TTC AAC CTG TGC GCC ATC AGC GTG GAC      499
Met Leu Cys Thr Ala Ser Ile Phe Asn Leu Cys Ala Ile Ser Val Asp
        120             125             130

AGG TTC GTG GCC GTG GCC GTG CCG CTG CGC TAC AAC CGG CAC GGT GGG      547
Arg Phe Val Ala Val Ala Val Pro Leu Arg Tyr Asn Arg Gln Gly Gly
    135             140             145

AGC CGC CGG CAG CTG CTC CTC ATC GGC GCC ACG TGG CTG CTG TCC GCG      595
Ser Arg Arg Gln Leu Leu Leu Ile Gly Ala Thr Trp Leu Leu Ser Ala
150             155             160

GCC GTG GCC GCC CCC GTA CTG TGC GGC CTC AAC GAC GTG CGC GGC CGC      643
Ala Val Ala Ala Pro Val Leu Cys Gly Leu Asn Asp Val Arg Gly Arg
165             170             175             180
```

FIG. 1C

```
CAC CCC GCC GTG TGC CGC CTG GAG GAC CGC GAC TAC GTG GTC TAC TCG    691
Asp Pro Ala Val Cys Arg Leu Glu Asp Arg Asp Tyr Val Val Tyr Ser
            185             190             195

TCC GTG TGC TCC TTC TTC CTA CCC TGC CCG CTC ATG CTG CTG TAC        739
Ser Val Cys Ser Phe Phe Leu Pro Cys Pro Leu Met Leu Leu Tyr
            200             205             210

TGG ACG TTC CGC TTC CGC GGC CTG CAG CGC TGG GAG GTG GCA CGT CGC GCC 787
Trp Thr Phe Arg Phe Arg Gly Leu Gln Arg Trp Glu Val Ala Arg Arg Ala
            215             220             225

AAG CTG CAC GGC CGC GCG GCC CGA CCC AGC GGC CCT GGC CCG CCT        835
Lys Leu His Gly Arg Ala Pro Arg Pro Ser Gly Pro Gly Pro Pro
            230             235             240

TCC CCC ACG CCA CCC GCG CGC CTC CCC CAG GAC CCC TGC GGC CCC        883
Ser Pro Thr Pro Pro Ala Arg Leu Pro Gln Asp Pro Cys Gly Pro
245             250             255             260

GAC TGT GCG CCC CCC GCG CCC GGC CTC CCG GAC CCC TGC GGC TCC        931
Asp Cys Ala Pro Pro Ala Pro Gly Leu Pro Asp Pro Cys Gly Ser
            265             270             275
```

FIG. 1D

```
AAC TGT GCT CCC CCC GAC GCC GTC AGA GCC GCG GCG CTC CCA CCC CAG    979
Asn Cys Ala Pro Pro Asp Ala Val Arg Ala Ala Ala Leu Pro Pro Gln
        280                 285                 290

ACT CCA CCG CAG ACC CGC AGG AGG CGT GCC AAG ATC ACC GGC CGG       1027
Thr Pro Pro Gln Thr Arg Arg Arg Arg Ala Lys Ile Thr Gly Arg
        295                 300                 305

GAC CGC AAG GCC ATG AGG GTC CTG CCG GTG GTC GTG GGG GCC TTC CTG   1075
Glu Arg Lys Ala Met Arg Val Leu Pro Val Val Val Gly Ala Phe Leu
        310                 315                 320

CTC TGC TGG ACG CCC TTC TTC GTC CAC ATC ACG CAC GTG CTG TGT       1123
Leu Cys Trp Thr Pro Phe Phe Val His Ile Thr Gln Ala Leu Cys
        325                 330                 335           340

CCT GCC TGC TCC GTG CCG CCG CGG CTG GTC AGC GCC GTC ACC TGG CTC   1171
Pro Ala Cys Ser Val Pro Pro Arg Leu Val Ser Ala Val Thr Trp Leu
        345                 350                 355

GGC TAC GTC AAC AGC GCC CTC ACC CCC GTC ATC TAC ACT GTC TTC AAC   1219
Gly Tyr Val Asn Ser Ala Leu Thr Pro Val Ile Tyr Thr Val Phe Asn
        360                 365                 370
```

FIG. 1E

```
GCC CAG TTC CCC AAC GTC TTC CGC AAG GCC CTG CGT GCC TGC TGC TGAGCCGGGC  1274
Ala Glu Phe Arg Asn Val Phe Arg Lys Ala Leu Arg Ala Cys Cys
        375                         380                     385

ACCCCCGGGAC GCCCCCCGGC CTCATGGCCA GGCCTCAGGG ACCAAGGAGA TGGGGAGGGC  1334

GCTTTTGTAC GTTAATTAAA CAAATTCCTT CCCAAA  1370
```

FIG. 2A

```
CGGGGGCGGG ACCAGGGTCC GGCCGGGGCG TGCCCCCGGG GAGGGACTCC CCGGCTTGCC        60

CCCCGGCGTT GTCCGCGGTG CTCAGCGCCC GCCCGGGCGC GCC ATG GGG AAC CGC        115
                                             Met Gly Asn Arg
                                              1

AGC ACC GCG GAC GCG GAC GGG CTG GCT GGG CGG GGG GCC GCG                163
Ser Thr Ala Asp Ala Asp Gly Leu Leu Ala Gly Arg Ala Ala
 5              10              15              20

GGG GCA TCT GCG GGG GCA TCT GCG GGG CTG GCT GGG CAG GGC GCG            211
Gly Ala Ser Ala Gly Ala Ser Ala Gly Leu Ala Gly Gln Gly Ala
             25              30              35

GCG CTG GTG GGG GGC GTG CTG CTC ATC GGC GCG GTG CTC GCG GGG AAC        259
Ala Leu Val Gly Gly Val Leu Leu Ile Gly Ala Val Leu Ala Gly Asn
             40              45              50

TCG CTC GTG TGC GTG AGC GTG GCC ACC GAG CGC GCC CTG CAG ACG CCC        307
Ser Leu Val Cys Val Ser Val Ala Thr Glu Arg Ala Leu Gln Thr Pro
 55              60              65

ACC AAC TCC TTC ATC GTG AGC CTG GCG GCC GCC GAC CTC CTC GCT            355
Thr Asn Ser Phe Ile Val Ser Leu Ala Ala Ala Asp Leu Leu Ala
 70              75              80
```

FIG. 2B

```
        CTC CTG GTG CTG CCG CTC TTC GTC TAC TCC GAG GTC CAG GGT GGC GCG   403
        Leu Leu Val Leu Pro Leu Phe Val Tyr Ser Glu Val Gln Gly Gly Ala
         85              90              95             100

TGG CTG CTG AGC CCC CGC CTG TGC GAC GCC ATG CTC ATG GCC ATG GAC GTC   451
        Trp Leu Leu Ser Pro Arg Leu Cys Asp Ala Met Leu Met Ala Met Asp Val
                       105             110             115

ATG CTG TGC ACC GCC TCC ATC TTC AAC CTG TGC GCC ATC AGC GTG GAC   499
        Met Leu Cys Thr Ala Ser Ile Phe Asn Leu Cys Ala Ile Ser Val Asp
                       120             125             130

AGG TTC GTG GCC GTG GCC CCG GTG CTG CGC TAC AAC CGG CAG GGT GGG   547
        Arg Phe Val Ala Val Ala Pro Val Leu Arg Tyr Asn Arg Gln Gly Gly
                135             140             145

AGC CGC CGG CAG CTG CTC CTG ATC GGC GCC ACG TGG CTG TCC GCG   595
        Ser Arg Arg Gln Leu Leu Leu Ile Gly Ala Thr Trp Leu Ser Ala
                150             155             160

GCG GTG GCG CCC GTA CTG TGC GGC CTC AAC CAC CTG CGC GGC CGC   643
        Ala Val Ala Pro Val Leu Cys Gly Leu Asn Asp Val Arg Gly Arg
                165             170             175             180
```

FIG. 2C

```
GAC CCC GCC GTG TGC CGC CTG GAG CAC CGC GAC TAC GTG GTC TAC TCG    691
Asp Pro Ala Val Cys Arg Leu Glu His Arg Asp Tyr Val Val Tyr Ser
185                 190                 195

TCC GTG TGC TCC TTC TTC CTA CCC TGC ATG CTC CCG CTG CTG TAC        739
Ser Val Cys Ser Phe Phe Leu Pro Cys Met Leu Pro Leu Leu Tyr
        200                 205                 210

TGG GCC ACG TTC CGC GGC CTG CAG CGC TGG GAG GTG GCA CGT CGC GCC    787
Trp Ala Thr Phe Arg Gly Leu Gln Arg Trp Glu Val Ala Arg Arg Ala
215                 220                 225

AAG CTG CAC GGC CGC GCG CCC CGA AGC GGC CCT GGC CCG CCT            835
Lys Leu His Gly Arg Ala Pro Arg Arg Ser Gly Pro Gly Pro Pro
230                 235                 240

TCC CCC ACG CCA CCC GCG CTC CAG GAC CCC TGC GGC CCC                883
Ser Pro Thr Pro Pro Ala Leu Gln Asp Pro Arg Leu Pro Cys Gly Pro
245                 250                 255                 260

GAC TGT GCG CCC CCC GGC CTT CCC GGT GGT CCC TGC GGC CCC            931
Asp Cys Ala Pro Pro Gly Leu Pro Arg Gly Pro Cys Gly Pro
265                 270                 275
```

FIG. 2D

```
GAC TGT GCG CCC GCC GCG CCC AGC CTC CCC CAG GAC CCC TGC GGC CCC      979
Asp Cys Ala Pro Ala Pro Ser Leu Pro Gln Asp Pro Cys Gly Pro
280             285             290

GAC TGT GCG CCC GCC CCC CTC GGC CCG GAC CCC TGC GGC TCC           1027
Asp Cys Ala Pro Ala Pro Leu Gly Pro Asp Pro Cys Gly Ser
295             300             305

AAC TGT GCT CCC CCC GAC GCC AGA GCC GCC GCG CTC CCA CCC CAC      1075
Asn Cys Ala Pro Pro Asp Val Arg Ala Ala Ala Leu Pro Pro Gln
310             315             320

ACT CCA CCG CAG ACC CGC AGG AGG CGT GCC AAG ATC ACC GGC CGG      1123
Thr Pro Pro Gln Thr Arg Arg Arg Arg Ala Lys Ile Thr Gly Arg
325             330             335             340

GAG CGC AAG GCC ATG AGG GTC CTG CCG GTG GTC GGG GCC TTC CTG      1171
Glu Arg Lys Ala Met Arg Val Leu Pro Val Val Gly Ala Phe Leu
345             350             355

CTG TGC ACG CCC TTC TTC GTG GTG CAC ATC ACG CAG GCG CTG TGT      1219
Leu Cys Trp Thr Pro Phe Phe Val Val His Ile Thr Gln Ala Leu Cys
360             365             370
```

FIG. 2E

```
CCT GCC TGC TCC CTG CCC CCG CTG GTC AGC GCC GTC ACC TGG CTG      1267
Pro Ala Cys Ser Leu Pro Pro Leu Val Ser Ala Val Thr Trp Leu
    375                 380                 385

GGC TAC GTC AAC AGC GCC CTC ACC CCC GTC ATC TAC ACT GTC TTC AAC  1315
Gly Tyr Val Asn Ser Ala Leu Thr Pro Val Ile Tyr Thr Val Phe Asn
        390                 395                 400

GCC GAG TTC CGC AAC GTC TTC CGC AAG GCC CTG CGT GCC TGC TGA GCCGGGC  1370
Ala Glu Phe Arg Asn Val Phe Arg Lys Ala Leu Arg Ala Cys Cys
405                 410                 415                 420

ACCCCCGGAC GCCCCCCGGC CTGATGGCCA GGCCTCAGGG ACCAAGGAGA TGGGGAGGGC  1430

GCTTTTGTAC GTTAATTAAA CAAATTCCTT CCCAAA                          1466
```

FIG. 3A

```
CGGGGGCGGG ACCAGGGTCC GGCCGGGGCG TGCCCCCGGG GAGGGACTCC CCGGGCTTGCC     60

CCCCGGCGTT GTCCGCGGTG CTCAGCGCCC GCCCGGGCGC GCC ATC GGG AAC CCC      115
                                              Met Gly Asn Arg
                                               1

AGC ACC GCG GAC GCG GAC GGG CTG GCT GGG CGC GGG CGG GCC GCG        163
Ser Thr Ala Asp Ala Asp Gly Leu Ala Gly Arg Gly Arg Ala Ala
 5              10              15              20

GGG GCA TCT GCG GGG GCA TCT GCG GGG CTG GCT GGG CAG GGC GCG GCG   211
Gly Ala Ser Ala Gly Ala Gly Ala Gly Leu Ala Gly Gln Gly Ala Ala
             25              30              35

GCG CTG GTG GGG GGC GTG CTC ATC GGC CTC GCG GTG CTC GCG GGG AAC   259
Ala Leu Val Gly Gly Val Leu Ile Gly Leu Ala Val Leu Ala Gly Asn
         40              45              50

TCG CTC GTG TGC GTG AGC GTG GCC ACC GAG CGC CTG CAG ACG CCC       307
Ser Leu Val Cys Val Ser Val Ala Thr Glu Arg Ala Leu Gln Thr Pro
         55              60              65

ACC AAC TCC TTC ATC GTG AGC CTG GCG GCC GAC CTC CTC CTC GCT       355
Thr Asn Ser Phe Ile Val Ser Leu Ala Ala Asp Leu Leu Leu Ala
 70              75              80
```

FIG. 3B

```
CTC CTG GTG CTG CCG CTC TTC GTC TAC TCC GAG GTC CAG GGT GGC GCG    403
Leu Leu Val Leu Pro Leu Phe Val Tyr Ser Glu Val Gln Gly Gly Ala
         85              90              95             100

TGG CTG CTG AGC CCC CGC CTG TGC GAC GCC CTC ATG GCC ATG GAC GTC    451
Trp Leu Leu Ser Pro Arg Leu Cys Asp Ala Leu Met Ala Met Asp Val
            105             110             115

ATG CTG TGC ACC GCC TCC ATC TTC AAC CTG TGC GCC ATC AGC GTG GAC    499
Met Leu Cys Thr Ala Ser Ile Phe Asn Leu Cys Ala Ile Ser Val Asp
            120             125             130

AGG TTC GTG GCC GTG CCG CTG CTC CGC TAC AAC CGG CAG GGT GGG        547
Arg Phe Val Ala Val Pro Leu Leu Arg Tyr Asn Arg Gln Gly Gly
        135             140             145

AGC CGC CGG CAG CTG CTC ATC GGC GCC ACG TGG CTC CTG TCC GCG        595
Ser Arg Arg Gln Leu Leu Ile Gly Ala Thr Trp Leu Leu Ser Ala
    150             155             160

GCG GCG GCC CCC GTA CTG TGC GGC CTC AAC GAC GTG CGC GGC CGC        643
Ala Val Ala Pro Val Leu Cys Gly Leu Asn Asp Val Arg Gly Arg
    165             170             175             180
```

FIG. 3C

```
GAC CCC GCC GTG TGC CGC CTG GAG GAC CGC GAC TAC GTG GTC TAC TCG    691
Asp Pro Ala Val Cys Arg Leu Glu Asp Arg Asp Tyr Val Val Tyr Ser
                185                 190                 195

TCC GTG TGC TCC TTC TTC CTA CCC TGC CTC ATG CTG CTG TAC            739
Ser Val Cys Ser Phe Phe Leu Pro Cys Leu Met Leu Leu Tyr
        200                 205                 210

TGG GCC ACG TTC CGC GGC CTG CAG CGC TGG GAG GTG GCA CGT CGC GCC    787
Trp Ala Thr Phe Arg Gly Leu Gln Arg Trp Glu Val Ala Arg Arg Ala
                215                 220                 225

AAG CTG CAC GGC CGC GCG CCC CGC CGA CCC AGC GGC CCT GGC CCG CCT    835
Lys Leu His Gly Arg Ala Pro Arg Arg Pro Ser Gly Pro Gly Pro Pro
                230                 235                 240

TCC CCC ACG CCA CCC GCG CCC CTC CCC CAG GAC CCC TGC GGC CCC        883
Ser Pro Thr Pro Pro Ala Pro Leu Pro Arg Leu Pro Gln Asp Pro Cys Gly Pro
245                 250                 255                 260

GAC TGT GCG CCC CCC GGC CTT CCC CGG GGT CCC TGC GGC CCC            931
Asp Cys Ala Pro Pro Gly Leu Pro Arg Gly Pro Cys Gly Pro
                265                 270                 275
```

FIG. 3D

```
GAC TGT GCG CCC     GCC GGC CTC CCC CCG     GAC CCC TGC GGC CCC            979
Asp Cys Ala Pro     Ala Pro Gly Leu Pro     Pro Asp Pro Cys Gly Pro
        280                 285                     290

GAC TGT GCG CCC CCC GCC GGC CTC CCC CAG CAC CCC TGC GGC CCC                1027
Asp Cys Ala Pro Pro Ala Pro Gly Leu Pro Gln Asp Pro Cys Gly Pro
        295             300             305

GAC TCT GCG CCC CCC GCC GGC CTT CCC CGG GGT CCC TGC GGC CCC                1075
Asp Cys Ala Pro Pro Ala Pro Gly Leu Pro Arg Gly Pro Cys Gly Pro
310             315             320

GAC TGT GCG CCC CCC GCC GGC CTC CCC CAG GAC CCC TGC GGC CCC                1123
Asp Cys Ala Pro Pro Ala Pro Gly Leu Pro Gln Asp Pro Cys Gly Pro
325             330             335             340

GAC TGT GCG CCC CCC GCC GGC CTC CCC CCG GAC CCC TGC GGC TCC                1171
Asp Cys Ala Pro Pro Ala Pro Gly Leu Pro Pro Asp Pro Cys Gly Ser
        345             350             355

AAC TGT GCT CCC GAC GCC GTC ACA GCC GCG CTC CCA CCC CAG                    1219
Asn Cys Ala Pro Asp Ala Val Arg Ala Ala Leu Pro Pro Gln
360             365             370
```

FIG. 3E

```
ACT CCA CAG ACC CGC AGG CGT GCC AAG ATC ACC GGC CGG     1267
Thr Pro Gln Thr Arg Arg Arg Ala Lys Ile Thr Gly Arg
        375             380             385

GAG CGC AAG GCC ATG AGG GTC CTG CCG GTG GTC TTC CTG     1315
Glu Arg Lys Ala Met Arg Val Leu Pro Val Val Phe Leu
        390             395             400

CTG TGC TGG ACG CCC TTC GTG GTG CAC ATC CAG GCG CTG TGT 1363
Leu Cys Trp Thr Pro Phe Val Val His Ile Gln Ala Leu Cys
405             410             415             420

CCT GCC TGC TCC GTG CCC CGG CTG GTC AGC GCC GTC ACC TGG CTG 1411
Pro Ala Cys Ser Val Pro Arg Leu Val Ser Ala Val Thr Trp Leu
            425             430             435

GGC TAC GTC AAC ACC GCC CTC ACC CCC GTC ATC TAC ACT GTC TTC AAC 1459
Gly Tyr Val Asn Thr Ala Leu Thr Pro Val Ile Tyr Thr Val Phe Asn
        440             445             450

GCC CAG TTC CGC AAC GTC TTC CGC AAG GCC CTG CGT GCC TGC TGC TGA GCCGGGC 1514
Ala Gln Phe Arg Asn Val Phe Arg Lys Ala Leu Arg Ala Cys Cys
        455             460             465
```

FIG. 3F

```
ACCCCCGGAC GCCCCCCGGC CTGATGGCCA GGCCTCAGGG ACCAAGGAGA TGGGGAGGGC    1574
GCTTTTGTAC GTTAATTAAA CAAATTCCTT CCCAAA                              1610
```

HUMAN D4 DOPAMINE RECEPTOR AND ITS USES

This invention was made with government support under NIMH grant MH-48991 awarded by the National Institutes of Health, Unites States of America. The government has certain rights in the invention.

This application is a continuation-in-part of U.S. patent application Ser. No. 07/928,611, filed on Aug. 10, 1992, which is a continuation-in-part of U.S. patent application Ser. No. 07/626,618, filed on Dec. 7, 1990, U.S. Pat. No. 5,422,265, both of which are hereby incorporated by reference.

BACKGROUND OF THE INVENTION

1. Field of the Invention

The invention relates to dopamine receptors from mammalian species and the genes corresponding to such receptors. In particular, it relates to the human dopamine receptor D4. Specifically, the invention relates to the construction of recombinant expression constructs capable of expressing the human D4 dopamine receptor in cultures of transformed eukaryotic cells and the production of human D4 dopamine receptor protein in such cultures. The invention relates to the use of such cultures of transformed eukaryotic cells producing the human D4 dopamine receptor for the characterization of antipsychotic drugs. 2. Description of the Related Art Dopamine is a neurotransmitter that participates in a variety of different functions mediated by the nervous system, including vision, movement, and behavior (see generally Cooper et al., 1978, *The Biochemical Basis of Neuropharmacology*, 3d ed., Oxford University Press, New York, pp. 161–195). The diverse physiological actions of dopamine are in turn mediated by its interaction with one of the five known types of G protein-coupled receptors (D 1, D2, D3, D4 and DS), which either stimulate or inhibit the enzyme adenylyl cyclase in response to dopamine binding (Kebabian & Calne, 1979, Nature 277: 93–96). Alterations in the number or activity of these receptors may be a contributory factor in human disease such as Parkinson's disease (a movement disorder) and schizophrenia (a behavioral disorder).

A great deal of information has accumulated on the biochemistry of the D1 and D2 dopamine receptors, the archetypal dopamine receptors and the first to be studied, and methods have been developed to solubilize and purify these receptor proteins (see Senogles et al., 1986, Biochemistry 25: 749–753; Sengoles et al., 1988, J. Biol. Chem. 263: 18996–19002; Gingrich et al., 1988, Biochemistry 27: 3907–3912); said methods have been adapted to study the other types of dopamine receptors as well.

The D1 dopamine receptor in several tissues appears to be a glycosylated membrane protein of about 72 kD (Amlalky et al., 1987, Mol. Pharmacol. 31: 129–134; Niznik et al., 1988, Biochemistry 27: 7594–7599). The D2 receptor has been suggested to have a higher molecular weight of about 90–150 kD (Amlalky & Caron, 1985, J. Biol. Chem. 260: 1983– 1986; Amlaiky & Caron, 1986, J. Neurochem. 47: 196–204; Jarvie et al., 1988, Mol. Pharmacol. 34: 91–97). A recently discovered additional dopamine receptor, termed D3 (Sokoloffet al., 1990, Nature 347: 146–151) has been shown to be expressed via an alternatively spliced mRNA, to produce proteins differing by the presence or absence of a 21 amino acid portion of the third cytoplasmic domain (Fishburn et al., 1993, J. Biol. Chem. 268: 5872–5878). Boundy et al. have used a baculovirus expression system to produce sufficient D3 protein to raise antibodies useful in immunoprecipitation and immunoblot assays of D3 receptor protein (1993, J. Pharmacol. Exper. Therap. 264: 1002–1011).

Dopamine receptors are primary targets in the clinical treatment of psychomotor disorders such as Parkinson's disease and affective disorders such as schizophrenia (Seeman et al., 1987, Neuropsychopharm. 1: 5–15; Seeman, 1987, Synapse 1: 152–333). The different dopamine receptors have been cloned as a result of nucleotide sequence homology between these receptor genes (Bunzow et al., 1988, Nature 336: 783–787; Grandy et al., 1989, Proc. Natl. Acad. Sci. USA 86: 9762–9766; Dal Toso et al., 1989, EMBO J. 8: 4025–4034; Zhou et al., 1990, Nature 346: 76–80; Sunahara et al., 1990, Nature 346: 80–83; Sokoloff et al., 1990, Nature 347: 146– 151; Van Tol et al., 1991, Nature 350: 610–614; Van Tol et al., 1992, Nature 358: 149–152; Sunahara et al., 1991, Nature 350: 614–619).

The antipsychotic clozapine is useful for socially withdrawn and treatment-resistant schizophrenics (see Kane et al., 1990, Nature 347: 146–151), but unlike other antipsychotic drugs, clozapine does not cause tardive dyskinesia (see Casey, 1989, Psychopharmacology 99: 547–553). Clozapine cannot exert its effects via the D2 or D3 receptors, however, because the dissociation constants of D2 and D3 for clozapine are 3 to 30-fold higher than the therapeutic free concentration of clozapine in plasma water (Ackenheil et al., 1976, Arzneim-Forsch 26: 1156–1158; Sandoz Canada, Inc., 1990, Clozaril: Summary of preclinical and clinical dam). This observation suggested the existence of dopamine receptors more sensitive to the antipsychotic clozapine than D2 or D3.

Some of the present inventors have isolated and characterized the gene for the only known clozapine-reponsive human dopamine receptor, D4 (see U.S. patent application Ser. Nos. 07/928,611 and 07/626,618, both incorporated by reference). The human D4 dopamine receptor gene displays a high degree of homology to the human dopamine D2 and D3 receptor genes. The pharmacological profile of the receptor protein encoded by and produced by expression of this gene also resembles the D2 and D3 receptors, but has 10-fold higher affinity for clozapine.

Some of the same present inventors have also discovered that the D4 gene is polymorphic in the human population, having at least 7 different alleles that can be detected by restriction fragment length polymorphism analysis (see, Botstein et al., 1980, Am. J. Hum. Genet. 32: 314–331). This is the first human receptor gene in the catecholamine receptor family which displays such polymorphic variations in the coding region. The observed polymorphism in dopamine D4 receptor genes may underlie individual differences in susceptibility to neuropsychiatric disorders such as schizophrenia and manic depression, as well as responsiveness to antipsychotic medication.

Expression of these varying alleles of this clozapine-sensitive dopamine receptor protein receptor provides a useful method for screening putative psychotopic drugs in vitro to enable the discovery of new types of drugs for treatment of human diseases such as schizophrenia, which may share clozapine's useful and advantageous properties of not inducing tardive dyskinesia and other motor side effects.

DESCRIPTION OF THE DRAWINGS

FIGS. 1A to 1E illustrates the nucleotide [SEQ ID No.: 1] and amino acid [SEQ ID No.:2] sequences of human D4 dopamine receptor allele D4.2.

FIGS. 2A to 2E illustrates the nucleotide [SEQ ID No.: 3] and amino acid [SEQ ID No.: 4] sequences of human D4 dopamine receptor allele D4.4.

FIGS. 3A to 3F illustrates the nucleotide [SEQ ID No.: 5] and amino acid [SEQ ID No.: 6] sequences of human D4 dopamine receptor allele D4.7.

SUMMARY OF THE INVENTION

Figure 4:
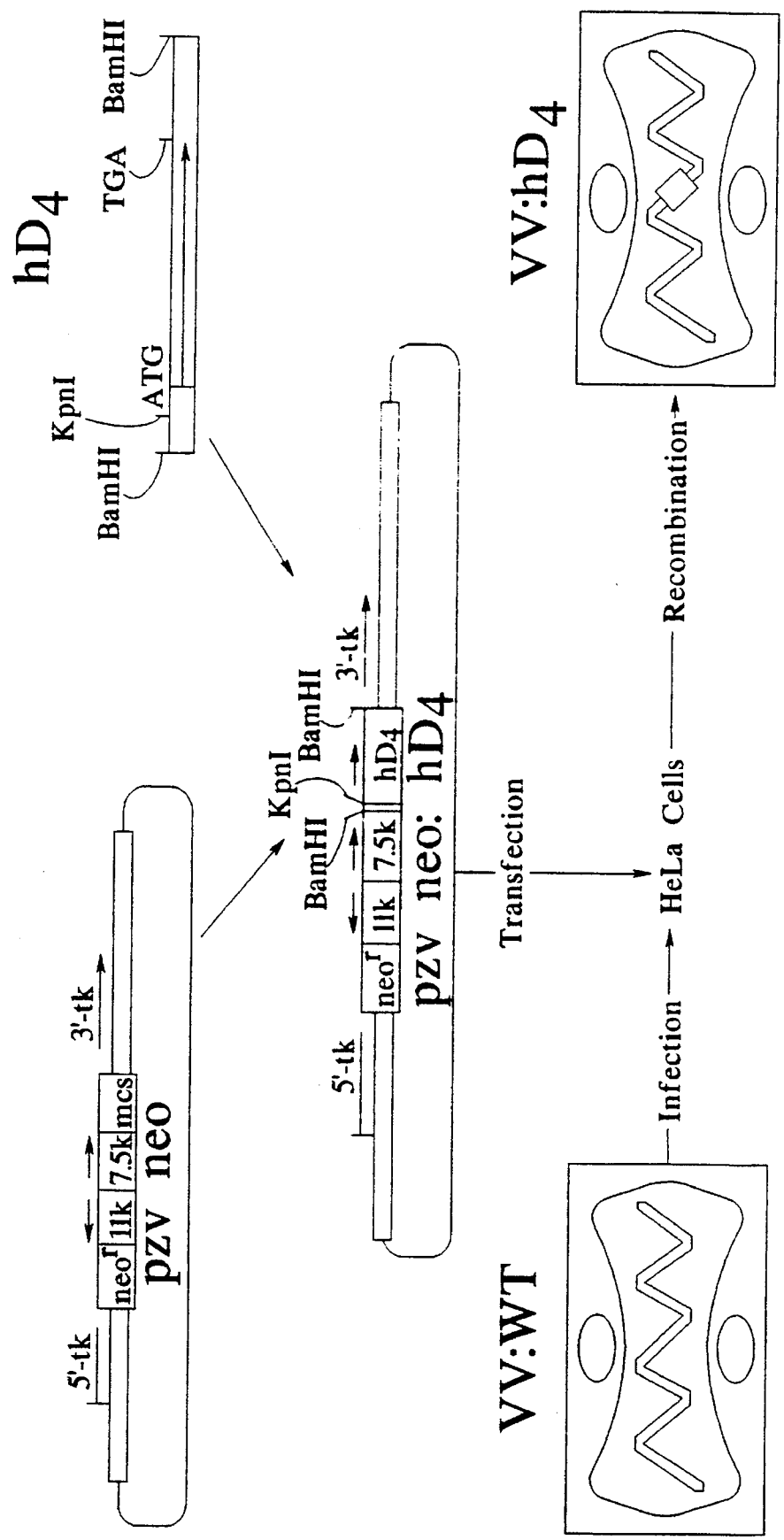
FIG. 4 schematically illustrates the construction of the vaccinia virus-based recombinant expression construct hD4.2.

The present invention is directed toward the isolation, characterization and pharmacological use of the human D4 dopamine receptor, the gene corresponding to this receptor, recombinant eukaryotic expression constructs capable of expressing the human D4 dopamine receptor in cultures of transformed eukaryotic cells and such cultures of transformed eukaryotic cells that synthesize the human D4 dopamine receptor.

It is an object of the invention to provide a nucleotide sequence encoding a mammalian dopamine receptor. Further, it is an object of the invention to provide a nucleotide sequence that encodes a mammalian dopamine receptor with novel and distinct pharmacological properties. It is specifically an object of the invention to provide a nucleotide sequence encoding a mammalian dopamine receptor having the particular drug dissociation properties of the human dopamine receptor D4. In particular, the mammalian dopamine receptor encoded by the nucleotide sequence of the present invention has a high affinity for the drug clozapine. The human D4 dopamine receptor embodied in the present invention shows a dissociation constant (termed $K_i$) of 1–40 nanomolar (nM), preferably 1–20 nM, most preferably 11 nM clozapine, as detected by the [$^3$H]spiperone binding assay disclosed herein. The human D4 dopamine receptor embodied in the present invention displays the following pharmacological profile of inhibition of [$^3$H]spiperone binding in the [$^3$H]spiperone binding assay: spiperone>eticlopride>clozapine>(+)-butaclamol>raclopride>SCH23390. In a preferred embodiment of the invention, the nucleotide sequence encoding a dopamine receptor encodes the human dopamine receptor D4.

The present invention provides a nucleic acid having a nucleotide sequence encoding a mammalian dopamine receptor that is the human D4 receptor. In preferred embodiments, this nucleotide sequence comprises cDNA sequences and genomic DNA sequences of naturally occurring alleles of the human D4 dopamine receptor, most preferably the cDNA sequences of the D4.2, D4.4 and D4.7 alleles (SEQ ID Nos.: 1, 3 & 5, respectively). The invention includes nucleic acid having a nucleotide sequence of allelic variations of this nucleotide sequence and the corresponding D4 receptor molecule, either naturally occurring or the product of in vitro chemical or genetic modification, having essentially the same nucleotide sequence as the nucleotide sequence of the human D4 receptor disclosed herein, wherein the resulting human D4 receptor molecule has substantially the same drug dissociation properties of the human D4 receptor molecule corresponding to the nucleotide sequence described herein. Allelic variations of this nucleotide sequence and the corresponding D4 receptor molecule, either naturally occurring or the product of in vitro chemical or genetic modification, having essentially the same nucleotide sequence as the nucleotide sequence of the human D4 receptor disclosed herein, wherein the resulting human D4 receptor molecule has substantially the same drug dissociation properties of the human D4 receptor molecule corresponding to the nucleotide sequence described herein are additional preferred embodiments of the invention. Specific preferred embodiments include alleles D4.2, D4.4 and D4.7 of the human D4 dopamine receptor gene, as defined herein and in co-pending U.S. patent application Ser. No. 07/928,611.

The invention also includes a predicted amino acid sequence for the human D4 dopamine receptor deduced from the nucleotide sequence comprising the complete coding sequence of the D4 dopamine receptor gene [SEQ ID Nos: 2,4 & 6]. Specific preferred embodiments comprise the amino acid sequence of the naturally-occurring alleles of the human D4 dopamine receptor gene. Allelic variations of this amino acid sequence and the corresponding D4 receptor molecule, either naturally occurring or the product of in vitro chemical or genetic modification, having essentially the same amino acid sequence as the human D4 receptor disclosed herein, wherein the human D4 receptor molecule has substantially the same drug dissociation properties of the human D4 receptor molecule corresponding to the amino acid sequence described herein are additional preferred embodiments of the invention. Specific preferred embodiments include the alleles D4.2, D4.4 and D4.7.

In addition, this invention includes recombinant DNA constructs comprising the human D4 dopamine receptor and sequences that mediate the replication and selected growth of microorganisms that carry this construct. In preferred embodiments, such DNA constructs comprise the recombinant vector pZVneo.

The present invention provides recombinant expression constructs comprising the nucleotide sequence of the human D4 dopamine receptor and sequences sufficient to direct the synthesis of the human D4 dopamine receptor protein in cultures of transformed eukaryotic cells. In preferred embodiments, the recombinant expression construct is comprised of plasmid sequences derived from a mammalian virus, most preferably vaccinia virus, and D4 dopamine receptor sequences corresponding to cDNA or genomic sequences for alleles D4.2, D4.4 and D4.7, as defined herein, as well as a hybrid human D4 dopamine gene, for example, as disclosed in co-pending U.S. patent application Serial No. 07/626,618, U.S. Pat. No. 5,422,265. Recombinant expression constructs of the invention also encompass embodiments comprising allelic variations of the human D4 dopamine receptor genomic DNA sequences and cDNA-derived sequences. This invention includes recombinant expression constructs comprising essentially the nucleotide sequences of genomic and cDNA clones of the human D4 dopamine receptor and allelic variations thereof in embodiments that provide for the expression of human D4 dopamine receptor protein in cultures of transformed eukaryotic cells. It is a particular advantage of the present invention that the vaccinia virus-based recombinant expression constructs of the invention have a wide host range and are capable of infecting most mammalin cell cultures known in the art.

It is also an object of this invention to provide cultures of transformed eukayotic cells that have been transformed with such recombinant expression constructs and that synthesize human D4 dopamine receptor protein. In a preferred embodiment, the invention provides monkey COS cells that synthesize human D4 dopamine receptor protein. In a particularly preferred embodiment, such cultures are produced by infection of said cells of said cultures with a recombinant human D4-vaccinia virus based construct, most preferably the construct hD4 described hereinbelow.

The present invention also includes membrane preparations comprising human D4 receptor protein, derived from cultures of mammalian cells transformed with the recombinant expression constructs of the invention. In a preferred embodiment, cell membranes containing human D4 dopamine receptor protein are isolated from cultures of Ltk cells infected with a vaccinia virus-based recombinant expression construct that directs the synthesis of human D4 dopamine receptor. It is a particular advantage of the present invention that the cultures of cells transformed with the recombinant expression constructs of the invention are capable of producing the D4 receptor protein on the surface of such transformed cells in amount corresponding to about 1 pmol/ mg membrane protein.

It also an object of this invention to provide the human D4 dopamine receptor for use in the in vitro screening of novel antipsychotic compounds. In a preferred embodiment, membrane preparations containing the human D4 dopamine receptor, derived from cultures of eukaryotic cells transformed with the recombinant expression constructs of the invention, are used to determine the drug dissociation properties of antipsychotic compounds in vitro. These properties are then used to characterize novel antipsychotic compounds by comparison to the binding properties of known antipsychotic compounds.

The present invention will also be useful for the detection of dopamine and dopamine analogues, known or unknown, either naturally occurring or as the embodiments of antipsychotic or other drugs.

It is an object of the present invention to provide a method for the quantitative detection of dopamine and dopamine analogues, either naturally occurring or as the embodiments of antipsychotic or other drugs. It is an additional object of the invention to provide a method to detect dopamine or dopamine analogues in blood, saliva, semen, cerebrospinal fluid, plasma, lymph, or any other bodily fluid.

Further uses of the invention include production of sufficient human dopamine D4 receptor protein to provide an effective antigenie inoculum for raising anti-D4 antisera in animals and in producing animal immune cells specific for human D4 epitopes for use in producing hybridomas producing anti-D4 monoclonal antibodies.

DETAILED DESCRIPTION OF THE PREFERRED EMBODIMENTS

The term "D4 dopamine receptor" as used herein refers to proteins substantially homologous to, and having substantially the same biological activity as, the protein coded for by the nucleotide sequences depicted in FIGS. 1A to 1E, 2A to 2E and 3A to 3F. (i.e., proteins which display high affinity binding to clozapine) [SEQ ID Nos: 1,3,& 5]. This definition is intended to encompass natural allelic variations in the D4 dopamine receptor sequence, specifically including the alleles D4.2, D4.4 and D4.7, as defined herein, and all references to the D4 dopamine receptor, and nucleotide and amino acid sequences thereof are intended to encompass such allelic variations, both naturally-occurring and man-made. Cloned genes of the present invention may code for D4 dopamine receptors of any species of origin, including, mouse, rat, rabbit, cat, and human, but preferably code for receptors of mammalian, most preferably human, origin.

The production of proteins such as the D4 dopamine receptor from cloned genes by genetic engineering is well known (see, e.g., U.S. Pat. No. 4,761,371 to Bell et al. at Col. 6 line 3 to Col. 9 line 65; the disclosure of all U.S. patent references cited herein is to be incorporated herein by reference). The discussion which follows is accordingly intended as an overview of this field, and is not intended to reflect the full state of the art.

DNA which encodes the D4 dopamine receptor may be obtained, in view of the instant disclosure, by chemical synthesis, by screening reverse transcripts of mRNA from appropriate tissues, cells or cell line cultures, by screening genomic libraries from appropriate cells, or by combinations of these procedures. Screening of mRNA or genomic DNA may be carded out with oligonucleotide probes generated from the D4 dopamine receptor gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, D4 dopamine receptor gene sequences may be obtained by use of the polymerase chain reaction (PCR) procedure, with the PCR oligonucleotide primers being produced from the D4-dopamine receptor gene sequence provided herein (see U.S. Pat. Nos. 4,683,195 to Mullis et al. and 4,683,202 to Mullis).

The D4 dopamine receptor may be synthesized in host cells transformed with constructs containing DNA encoding the D4 dopamine receptor. For the purposes of this invention, the term "transformed" is intended to encompass any method for introducing recombinant expression constructs of the invention into mammalian cells, including but not limited to transfection, electroporation, microinjection, osmotic shock, receptor endocytosis and most preferably, infection via viral-mediated mechanisms. The constructs of the invention are replicable and are used herein either to amplify DNA encoding the D4 dopamine receptor and/or to express DNA which encodes the D4 dopamine receptor. An expression construct is a replicahie DNA construct in which a DNA sequence encoding the D4 receptor is operably linked to suitable control sequences capable of effecting the expression of the D4 receptor in a suitable host. The need for such control sequences will vary depending upon the host selected and the transfection method chosen. Generally, control sequences include a transcriptional promoter, an optional operator sequence to control transcription, a sequence encoding suitable mRNA ribosomal binding sites, and sequences which control the termination of transcription and translation. When used for DNA amplification such constructs do not require expression control domains. All that is needed is the ability to replicate in a host, usually conferred by an origin of replication, and a selective marker gene to facilitate recognition of transformants.

Constructs useful for practicing the present invention include plasmids, viruses (including phage), retroviruses, and integratable DNA fragments (i.e., fragments integratable into the host genome by homologous recombination). The construct may replicate and function independently of the host genome, or may, in some instances, integrate into the host genome itself. Suitable constructs will contain replicon and control sequences which are derived from species compatible with the intended expression host. Preferred recombinant expression constructs comprise a nucleic acid consisting essentially of genomic or cDNA sequences of an allele of human D4, operatively linked to a nucleic acid comprising sequences derived from vaccinia virus.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in the same translational reading frame.

Transformed host cells are cells which have been transformed, transfected or infected with the D4 receptor-containing constructs assembled using recombinant DNA techniques. Transformed host cells ordinarily express the D4 receptor, but host cells transformed for purposes of cloning or amplifying the D4 receptor DNA need not express the D4 receptor. When expressed, the D4 receptor will typically be located in the host cell membrane.

Cultures of cells derived from multicellular organisms are a desirable host for recombinant D4 dopamine receptor synthesis. In principal, any higher eukaryotic cell culture can be used, whether from vertebrate or invertebrate culture. However, mammalian cells are preferred, as illustrated in the Examples. Propagation of such cells in cell culture has become a routine procedure (see Tissue Culture, Academic Press: New York (Kruse & Patterson, eds.) 1973). Examples of useful host cell lines are VERO cells, HeLa cells, Chinese hamster ovary (CHO) cells, and WI138, BHK, COS-7, CV, and MDCK cell lines. Preferred cells are mouse Ltk⁻ cells.

Expression constructs for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence. In preferred embodiments, these functionalities are provided by a nucleic acid derived from vaccinia virus DNA. Alterative embodiments comprise transcriptional and translational control sequences provided by other viral sources, such as baculovirus, polyomavirus, adenovirus, and simian virus 40 (SV40; see, e.g., U.S. Pat. No. 4,599,308). In additional alternatives, the human genomic D4 receptor promoter, control and/or signal sequences, may also be used, provided such control sequences are compatible with the host cell chosen.

D4 dopamine receptors made from cloned genes in accordance with the present invention may be used for screening compounds for D4 dopamine receptor activity, or for determining the amount of a dopaminergic drug in a solution (e.g., blood plasma or serum). For example, host cells may be transformed with a construct of the present invention, D4 dopamine receptors expressed in that host, the cells lysed, and the membranes from those cells used to screen compounds for D4 dopamine receptor binding activity. Competitive binding assays in which such procedures may be carried out are well known, as illustrated by the Examples below. By selection of host cells which do not ordinarily express a dopamine receptor, pure preparations of membranes containing D4 receptors can be obtained. Further, D4 dopamine receptor agonist and antagonists can be identified by transforming host cells with constructs of the present invention. Membranes obtained from such cells can be used in binding studies wherein the drug dissociation constants are measured. Such cells must contain D4 protein in the plasma and other cell membranes. Procedures for carrying out assays such as these are also described in greater detail in the Examples which follow.

Cloned genes and constructs of the present invention are useful to transform cells which do not ordinarily express the D4 dopamine receptor to thereafter express this receptor. Such cells are useful as intermediates for making cell membrane preparations for receptor binding assays, which are in turn useful for drug screening.

The Examples which follow are illustrative of specific embodiments of the invention, and various uses thereof. They are set forth for explanatory purposes only, and are not to be taken as limiting the invention.

EXAMPLE 1

Isolation and Characterization of Human D4 Dopamine Receptor Alelles

The isolation, nucleotide sequencing, analytical expression using SV40-based recombinant expression constructs, and biochemical characterization of the dopamine receptor proteins produced therefrom in mammalian cell culture transformed with such recombinant expression constructs, is described more fully in U.S. patent applications, Ser. Nos. 07/626,618, U.S. Pat. No. 5,422,265, and 07/928,611, hereby incorporated by reference. The nucleotide and amino acid sequences of human D4 receptor alleles D4.2 [SEQ ID Nos.: 1 & 2], D4.4 [SEQ ID Nos: 3 & 4] and D4.7 [SEQ ID Nos.: 5 & 6] are presented in FIGS. 1A to 1E, 2A to 2E and 3A to 3F, respectively.

EXAMPLE 2

Construction of Vaccinia Virus-Based Recombinant Expression Constructs for Expressing Human D4 Receptor Protein in Mammalian Cells In order to provide transformed culture of mammalian cells expressing the human D4 receptor protein, vaccinia virus-based recombinant expression constructs were produced as follows using methods well known in the art (see Sambrook et al., 1989, *Molecular Cloning: A Laboratory Manual,* 2d ed., Cold Spring Harbor Laboratory Press: New York). A schematic drawing of the cloning strategy is shown in FIG. 4.

A full-length human D4 dopamine receptor eDNA clone encoding the D4.4 allde (see van Tol et al., 1992, Nature 358: 149–152 and U.S. patent application Ser. No. 07/928, 611, filed Aug. 10, 1992) was digested with BamHI to liberate the eDNA sequences. The eDNA sequences were then ligated into the vaccinia virus recombination vector pZVneo using methods known in the an (Sambrook et al., ibid.). Recombinant clones containing the D4 sequences oriented properly for expression were determined by restriction enzyme mapping. Similar recombinant constructs are produced from clones encoding the D4.2 and D4.7 alleles.

One such construct, pZVneo.hD4.4, was then transfected into a culture of human HeLa cells previously infected with wild-type vaccinia virus. HeLa cells were grown in minimal esential media (MEM; GIBCO, Long Island, N.Y.) supplemented with 10% heat-inactivated fetal calf serum (FCS; GIBCO) to approximately 50% confluency in 100cm culture dishes (Falcon, Lincoln Park, N.J.). The cells were then trypsinized with a solution of 0.05 % trypsin in versine (phopshate buffered saline+1 mM ethylenediamine tetraacetic acid (EDTA)+0.0075 % phenol red) by incubating for about 1 min at 37° C. To each plate was added 1 mL of DMEM, and a 100μL aliquot was then mixed with trypan blue (GIBCO) and the number of viable cells/mL determined using a hemocytometer and phase-contrast microscopy. HeLa cells were then plated at a density of $5\times10^5$ cells/4 cm dish and incubated at 37° C. The cells were allowed to attach to the dish, and then were rinsed with PBS-MB (phosphate buffered saline+1 mM $MgCl_2$+ 0.1% bovine serum albumin at 4° C. Wild-type vaccinia virus was then added to each 4 cm dish at a concentration of 0.5–1 plaque-forming units (pfu)/cell and incubated 0.5–1h at room temperature.

After incubation, the PBS-MB was removed and each dish washed three times with DMEM (without serum supplement). 1 mL of DMEM was then added per dish and 100μL of a mixture containing 5μg pZVneo-hD4 and lipofectin (GIBCO) was added dropwise as the plates were gently rocked to mix. The plates were then incubated for 3h at 37° C. The transfection mixture was then removed and the cells re-fed with DMEM/10% FCS suplemented with 25μg/mL gentamycin (GIBCO) and incubated at 37° C. overnight.

The next day, the cells were harvested and virus liberated using a freeze-thaw regimen with sonication. The cells were harvested using a rubber policeman and transferred to a 50 mL centrifuge tube (Falcon, Cat.//2098). Cells were pelleted by low speed centrifugation (i.e., at 1000–1500 rpm for 5 min in a Sorvall Model RT6000B tabletop centrifuge). The pelleted cells were washed with PBS-M (phosphate buffered saline+1 mM $MgCl_2$) and repelleted. The cells were then resuspended in 1.0 mL PBS-M and subjected to alternative cycles of rapid freezing and thawing (preferably by immersion in dry ice/ethanol to freeze and a water bath at 37°–50° C. to thaw) for a total of three cycles. This crude virus suspension can be then frozen at −70° C. until further use, and was used to prepare plaque-purified D4-recombinant vaccinia virus-based recombinant expression constructs as described in Example 3 below.

EXAMPLE 3

Plaque Purification of Vaccinia Virus-Based Recombinant Expression Constructs Recombinant vaccinia virus containing hD4 sequences were plaque purified by infection of BSC-40 cells with the crude virus suspension described in Example 2 above. Such crude suspensions are assumed to have a titre of $5.0\times10^7$ pfu/mL. Several 100 mm plates of BSC-40 cells were prepared at the same time prior to infection so that at least one of the plates could be sacrificed to determine the number of cells/plate. Just prior to infection, media was removed and each plate rinsed with PBS-M. Virus was added at the desired multiplicity of infection (0.5– 1 pfu/cell) in an amount of PBS-M just sufficient to cover the surface of the culture dish. The virus aliquot was thawed just prior to infection and added to PBS-M in a polypropylene tube. Just prior to addition to the culture dishes, the virus suspension in PBS-M was either vortexed to sonicated (twice for 10 min) to break up virus aggregates. The virus suspension was then added to each culture dish and the dish gently rocked to ensure even distribution of the virus innoculum. The innoculated cells were kept at room temperature for 0.5–1h with gentle rocking every 5–10 min. Thereafter, the innoculum was removed and the cells re-fed with culture media (MEM/10% FCS) and incubated at 37° C. under the usual culture conditions for 16–48h.

For plaque purification assays, a series of plates corresponding to 1000, 100 and 10 plaques were prepared as described above on the assumption that the crude virus suspension contained $10^7$ pfu/mL. Plaque lifts were performed 48h after infection of BSC-40 cells as follows. Three hours before lifting plaques onto filters, 400μL of a 1% solution of neutral red were added to each 100 mM dish and incubated at 37° C. until plaques became visible. For each dish, media was removed and a nylon or nitrocellulose filter [Nytran,(HA85 nitrocellulose, 0.45μm) Shleicher and Schuell, Keene, NH] was carefully placed on the cell monolayer using gloved hands. A tissue (Kimwipe, Kimberly-Clarke, Roswell, Calif.) wetted with PBS-M was used to gently press the filter against the monolayer, taking care not to smear the plaques by sliding over the monolayer. The filter was then separated from the monolayer using a forceps and laid plaque-side up on a piece of Whatman 3MM paper (Whatman, Gladstone, UK) wetted with PBS-MB in a 100 mM petri dish.

Next, a nitrocellulose filter (Shleicher & Schuell HA85) was carefully laid atop the first filter using gloved hands, and a Kimwipe wetted with PBS-MB used to carefully press the two filters together. The two filters were oriented to each other by asymetrically marking the filters using a paper punch sterilized with ethanol. The filters were separated using forceps and the second (nitrocellulose) filter placed on a piece of 3MM paper wetted with PBS-M in a 100 mm petri dish and stored at −70° C. until further use.

The first filter was used for identifying virus plaques produced by hD4-containing recombinant virus by nucleic acid hybridization using methods well known in the art (see Sambrook et al., ibid. ). First, each filter was floated on a volume of denaturing solution (0.5M NaOH/1.5M NaCl) for 10 min. The filter was then floated twice for 2 min on a volume of neutralization solution (0.5M Tris-HCl, pH 7.5/ 3.0M NaCl). The filters were then washed once in 2X standard saline citrate (SSC; 1X SSC=0.015M sodium citrate, pH 7.0/0.15M NaCl) and baked for 1–2h at 80° C. (or 20–30 min at 80° C. in vacuo). Filters thus prepared be stored at room temperature until use.

For hybridization assays, the filters were prepared as follows. Filters were placed in sufficient volume of proteinase K treatment buffer [50μg/mL freshly added proteinase K in 100 mM Tris-HCl (pH 8.0)/150 mM NaCl/10 mM EDTA/ 0.2% sodium dodecyl sulfate (SDS)] to completely cover them. The filters were then incubated at 50–55° C. for 30 min. The filters were then removed from this solution and placed in a sealable plastic bag with an excess of prehybridization solution [50% formamide/0.1M NaCl/10% dextran/1% SDS/25μg/mL denatured salmon sperm DNA] and incubated at 37° C. for 2–4h. The filters were then hybridized overnight in the same buffer containing an amount of radioactively-labeled (usually [32P]-dCTP-labeled) nucleic acid hybridization probe specific for human D4 dopamine receptor sequences (made using means well known in the art; see Sambrook et al., ibid.). After hybridization, probe solution was removed and the filters washed sequentially as follows: first, for 10 min at room temperature in 2X SSC; next, for 30–60 min at 65° C. in 2X SSC/1% SDS; and lastly for 10–30 min at room temperature in 0.1X SSC. The filters were wrapped in plastic film and placed under X-ray film (Kodak XAR-5, Rochester, NY) at −70° C. for a time appropriate for visuallizing D4-positive plaques.

Plaques were isolated for further plaque purification as follows. After visuallizing the D4-positive plaques by developing the X-ray film described above, the second set of nitrocellulose filters were oriented to the image from their cognate first filter using the previous asymmetric paper punch code. An area of nitrocellulose corresponding to each of a multiplicity of D4-positive plaques was removed from the second nitrocellulose filter (preferably using an ethanol-sterilized paper punch). Each such nitrocellulose dot was placed in a plastic tube (Falcon Cat. #2063) to which was added 200μL PBS-MB. The tubes were vortexed and/or sonicated for 1 min and subjected to 3 rounds of freeze/thaw. Virus was then grown from each isolated plaque by infection of BSC-40 cells as described above using 100μL of each plaque suspension; the remaining 100μL was stored at −70° C. Further rounds of plaque purification were performed essentially as described herein until every plaque was D4-positive in the hybridization assay. Plaque-pure suspensions were then used to prepare virus stocks of D4 recombinant phage as described in Example 4 below.

EXAMPLE 4

Production of Purified Stocks of Recombinant Human D4 Dopamine Receptor-Containing Vaccinia Virus As a final step in the plaque purification protocol described in Example 3 above, assays were also performed using an agar overlay technique. In this assay, following plaque-purified virus adsorption to cells on 100 mm plates, 10 mL of a mixture of 0.75% agar (SeaPlaque, FMC Corp. Rockland, Me.) in MEM/10%FCS was added to each plate and allowed to harden at room temperature for 15 min. Infected cells were then incubated under the usual conditions at 37° C. for 48h. The infected dishes were then treated by the addition of 5mL of a 1% solution of agar in water containing 200μL of a solution of 1% neutral red. The agar was again allowed to cool for 15 min at room temperature and the cells incubated at 37° C. for 2–3h to allow the dye to stain the cells. (Plaques appear as clear spots in red-stained cell monolayer). Plaques were then isolated by impaling an agar plug over the plaque with a Pasteur pipette and aspirating the plug into the pipette tip. Each agar plug was then expelled from the pipette into 200μL PBS-M in a 4 mL plastic tube (Falcon Cat #2063), and subjected to freeze/thaw disruption to liberate recombinant virus.

Large-scale preparations of plaque-purified D4-recombinant virus prepared as described herein, with the exception that plaque-purified infections were performed at a multiplicity of infection of 0.005 pfu/cell. BSC-40 cells were grown to confluency on 5 150mm culture dishes. The number of cells on one plate were counted to provide an estimate of the number of cells on the other 4 plates. Plaque-purified, titred virus stock was thawed, vortexed and/or sonicated briefly (10 sec) and placed on ice. Sufficient virus was added to 12 mL cold PBS-MB to correspond to 0.005 pfu/cell and 3mL/plate. Cells prepared for infection by removing media and washing once with warm PBS-MB. This solution was removed and 3mL of cold PBS-MB containing virus was added per plate. Virus was allowed to adsorb for 30 min at room temperature with gentle rocking every 5–10 min. The virus innoculum was then removed and each of the dishes re-fed with 20mL MEM + 10% heat-inactivated FCS. Cells were incubated for 48–72h at 37° C.

Virus was isolated by scraping the cells (still in culture media) using a rubber policeman. The cell suspension was then transferred to a 50 mL conical plastic centrifuge tube (Falcon Cat #2098). The cells were pelleted by low speed centrifugation as described above in Example 2 and resuspended in 10 mL PBS-MB. The cells were re-pelleted and then resuspended in 5 mL of a cold solution of 10 mM Tris (pH 9.0) and placed on ice. All steps hereinafter in this preparation were performed on ice. The cell suspension was then placed in a chilled Dounce homogenizer (Kontes Pestel A) and disrupted by 25 strokes. The disrupted cell suspension was transferred to a 15 ml screw-cap tube (Sarstedt, Newton, N.C.) and cell debris pelleted at 4° C. for 5 min at 2000 rpm in a Sorvall RT6000B centrifuge. The supernatant was transferred to a Beckman SW28 ultracentrifuge tube, and the pellet resuspended in 5 mL ice-cold 10 mM Tris (pH 9.0) and repelleted. The supernatant from this second low-speed centrifugation was pooled with the first supernatant.

The pooled supernatant was underlayed with 16 mL of a 36 % sucrose solution prepared in 10 mM Tris (pH 9.0). The supernatant was then ultracentrifuged at 18,000 rpm in a Beckman SW28 rotor for 80 min at 4° C. to pellet recombinant virus. After ultracentrifugation, the supernatant was removed from the visible virus pellet by aspiration, and the pellet resuspended in 1.0–1.5 mL 10 mm Tris (pH 9.0). This suspension was dounced about 7 times on ice to provide a suspension having a milky, even consistency. The recombinant virus suspension was then transferred in 20–40μL aliquots to 2 mL plastic screw-capped FALCON tubes, titred and stored at −70° C. Typical virus stocks prepared in this way were found to have viral titres of about $10^{10}$ pfu/mL.

EXAMPLE 5

Production of Human D4 Dopamine Receptor Protein in Mammalian Cell Cultures

Human D4 dopamine receptor protein was produced in mammalian cell cultures using the recombinant expression construct described in Example 2. Briefly, a culture of $10^6$ mouse Ltk⁻ cells (that do not produce an endogenous dopamine receptor) were infected with plaquepurified human D4 receptor-vaccinia virus recombinant expression construct as described above at a multiplicity of infection of 5 pfu/cell. Cells were harvested 16h after infection and a crude plasma membrane preparation prepared essentially as described in Zhou et al. [1990, Nature 347: 76–79] and co-pending U.S. patent application Ser. No. 07/928,611. Briefly, cells were harvested and homogenized using a teflon pestle in 50 mM Tris-HCl (pH 7.4 at 4° C.) buffer containing 5 mM EDTA, 1.5 mM $CaCl_2$, 5 mM $MgCl_2$, 5 mM KCl and 120 mM NaCl. Homogenates were pelleted by centrifugation at 800 g for 10 min, re-homogenized and re-pelleted, and then the supernatant fluid ultracentrifuged at 100,000 g for 30–60 min at 4° C. The resulting pellets were resuspended in buffer at a concentration of 150–250 μg/ml. Membrane preparations were stored at −80° C. until use in ligand binding experiments, as described below.

EXAMPLE 6

Analysis of Dopamine and Dopamine-Antagonist Binding of D4 Dopamine Receptor

Figure 5:
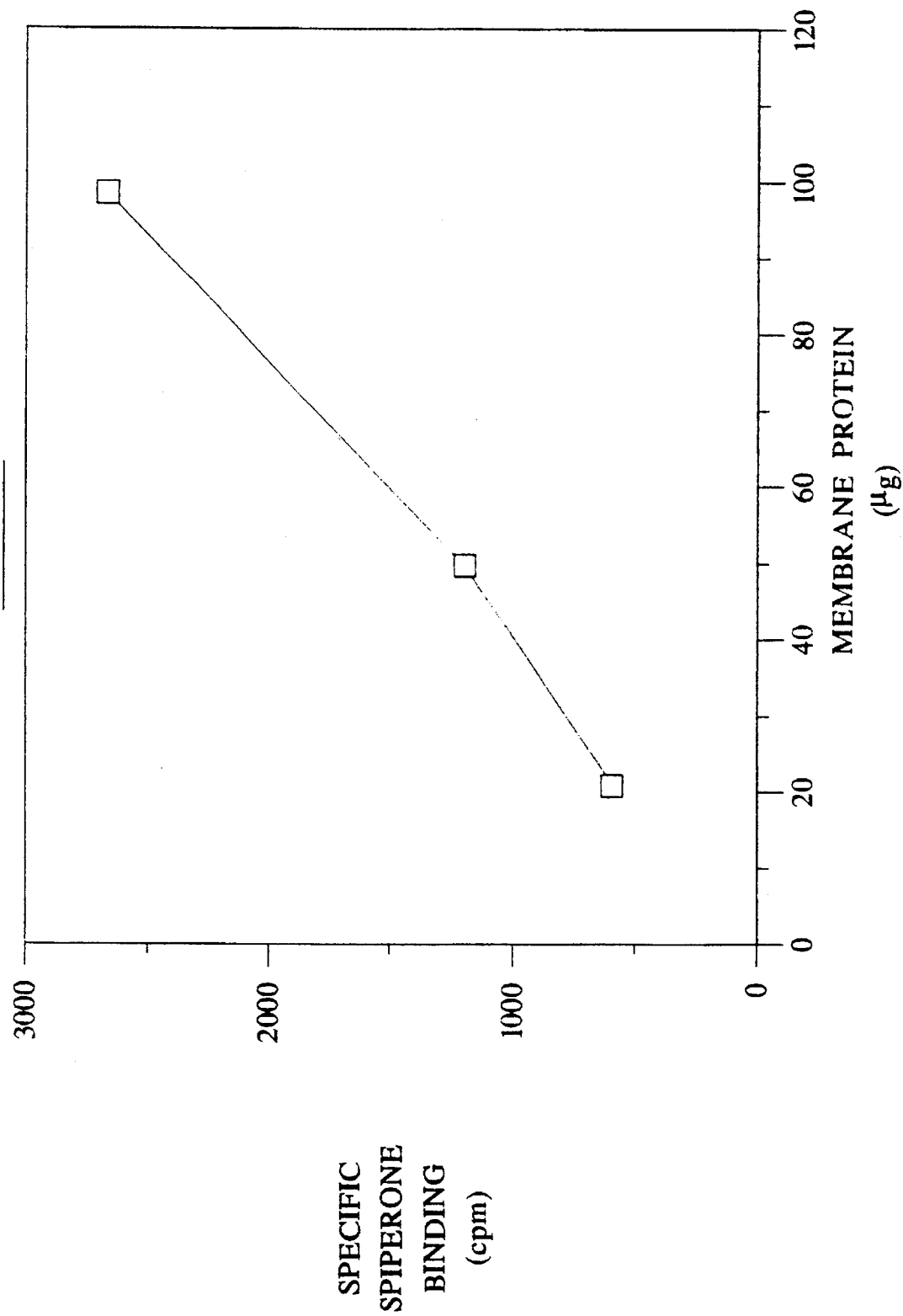
FIG. 5 shows the binding of [$^3$H]spiperone to membranes of cells infected with the vaccinia virus-based recombinant expression construct hD4.2.
Figure 6:
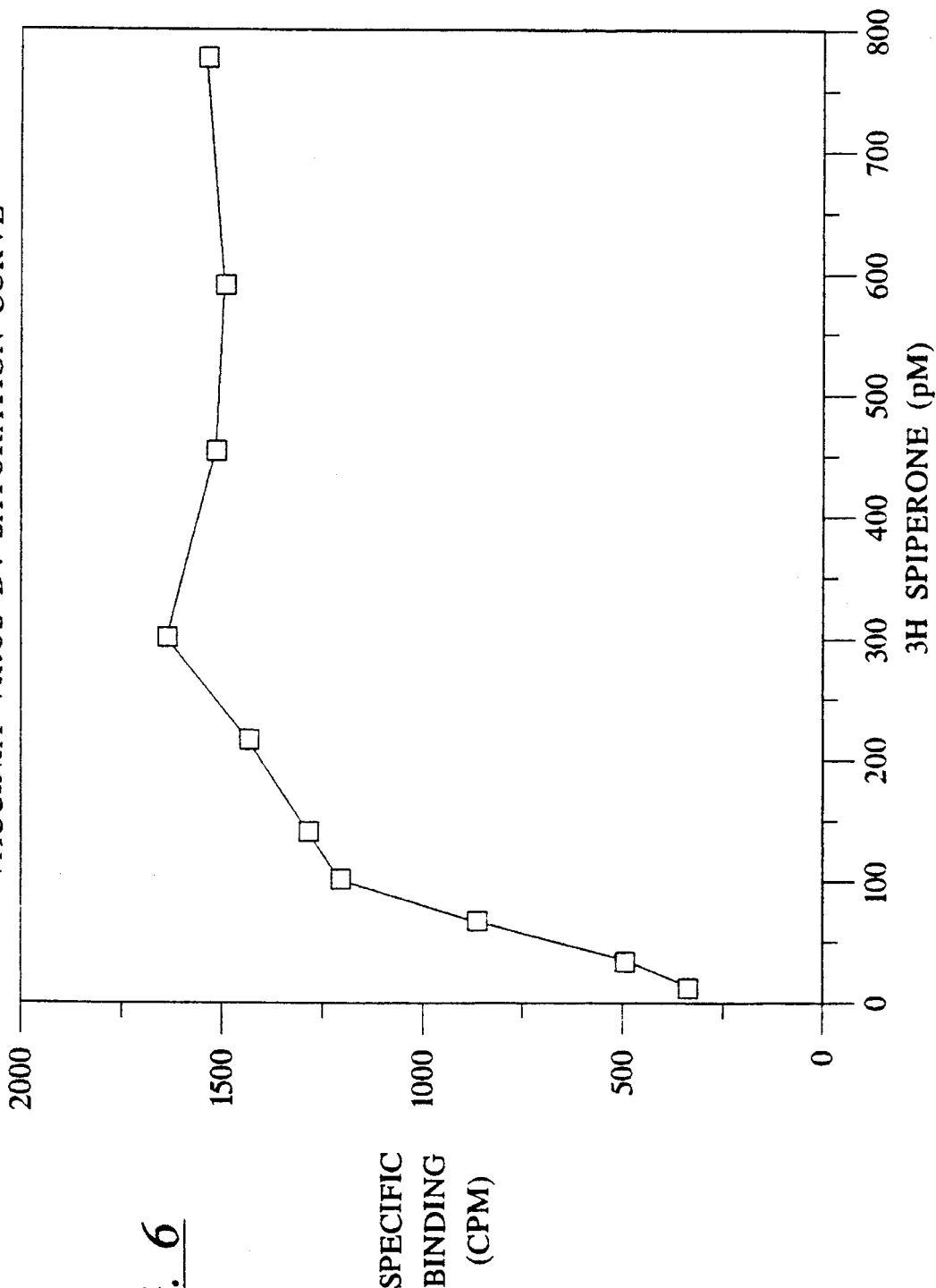
FIG. 6 demonstrates the pharmacological specificity of [$^3$H]spiperone binding to membranes of cells infected with the vaccinia virus-based recombinant expression construct hD4.2.

Ligand binding experiments were performed essentially as described in Bunzow et al. [1988, Nature 336: 783–787] and in co-pending U.S. patent application Ser. No. 07/928, 611. In binding experiments, increasing amounts of membrane protein was incubated with [³H]spiperone (70.3 Ci/mmol; 10–3000 pM final concentration) for 120 min at 22° C. in a total volume of 1 ml. The results of these experiments are shown in FIGS. 5 and 6. The results shown are representative of two independent experiments each conducted in duplicate. The results show specific binding that increases to saturation with increased membrane protein concentration. These results confirm that the infected cell cultures produce human D4 protein.

Figure 7:
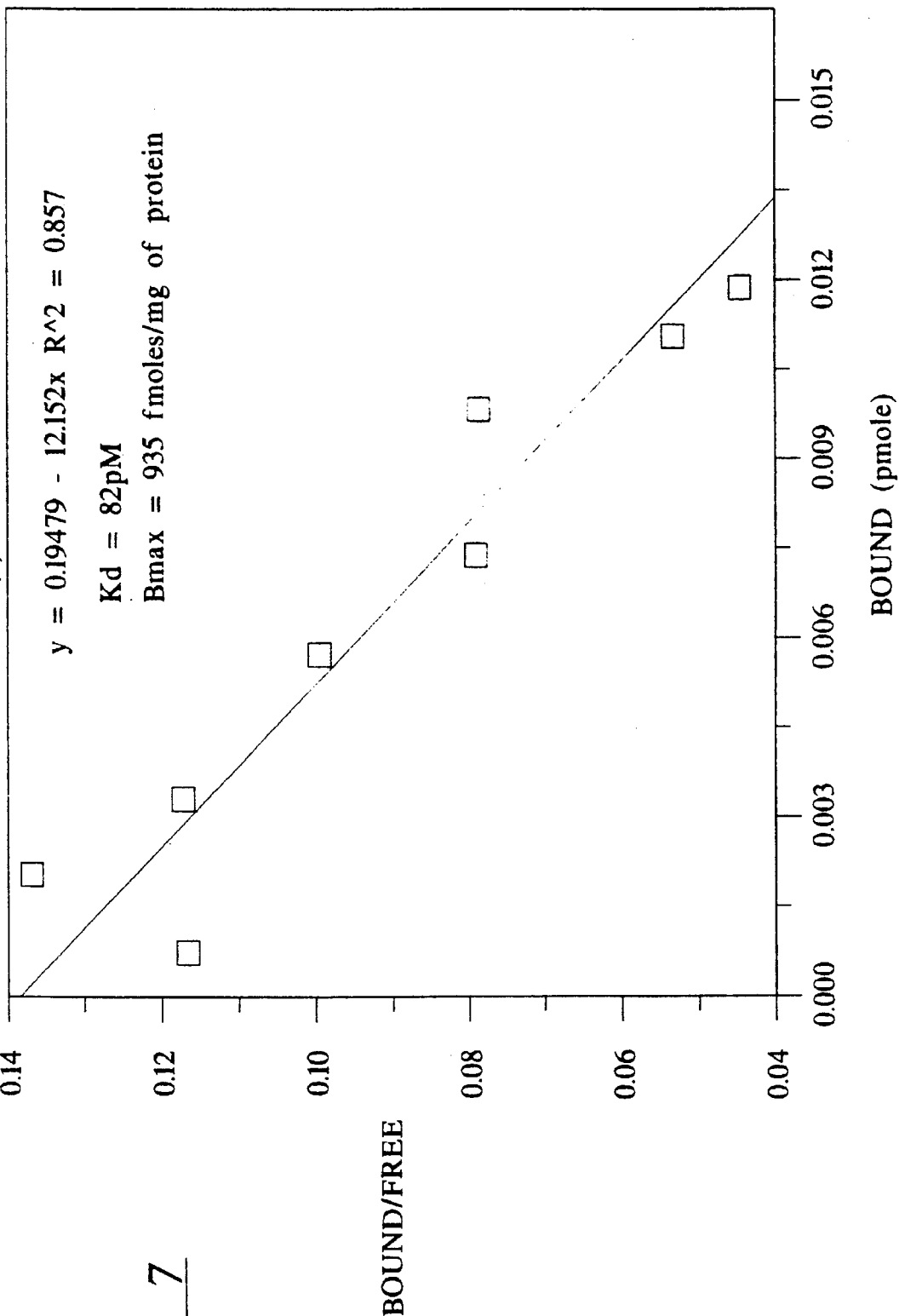
FIG. 7 illustrates Scatchard analysis of pharmacological data on specificity of [$^3$H]spiperone binding to membranes of cells infected with the vaccinia virus-based recombinant expression construct hD4.2.

For Scatchard analysis experiments, 0.25 ml aliquots of crude plasma membrane homogenate from hD4 recombinant vaccinia virus-infected cell cultures was incubated in duplicate with increasing concentrations of [$^3$H]spiperone (70.3 Ci/mmol; 10–3000 pM final concentration) under conditions described above. The estimated value for $B_{max}$ was derived from these data were obtained using the LIGAND computer program. A representative experiment is illustrated in FIG. 6, showing saturable spiperone binding with a $K_d$=68 pM (in good agreement with previously-obtained values of about 70 pM; Van Tol et al., 1991, Nature 350: 610–614 and co-pending U.S. patent application Ser. No. 07/928,611 ). Scatchard analysis of these data is shown in FIG. 7. The results of these experiments show a nearly 10-fold increase in $B_{max}$ (approximately 935 fmol/mg protein) over the values obtained using other recombinant expression constructs for human D4 (see co-pending U.S. patent applications Ser. Nos. 07/626,618, U.S. Pat. No. 5,422,265, and 07/928,611 ). These results demonstrate that the instant invention provides a means for producing significantly more D4 receptor protein in cultures of cells trasnformed with the vaccinia virus-based recombinant expression constructs described herein. These results make the instant invention useful in methods for screening novel psychotropic and anti-psychotic drugs for treatment of human diseases related to dopamine and dopamine receptor binding in vivo.

It should be understood that the foregoing disclosure emphasizes certain specific embodiments of the invention and that all modifications or alternatives equivalent thereto are within the spirit and scope of the invention as set forth in the appended claims.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 1370 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: 5'UTR
( B ) LOCATION: 1..103

( i x ) FEATURE:
( A ) NAME/KEY: 3'UTR
( B ) LOCATION: 1268..1370

( i x ) FEATURE:
( A ) NAME/KEY: CDS
( B ) LOCATION: 104..1267

( x i ) SEQUENCE DESCRIPTION: SEQ ID NO:1:

```
CGGGGGCGGG  ACCAGGGTCC  GGCCGGGGCG  TGCCCCCGGG  GAGGGACTCC  CCGGCTTGCC                    60

CCCCGGCGTT  GTCCGCGGTG  CTCAGCGCCC  GCCCGGGCGC  GCC ATG GGG AAC CGC                      115
                                                    Met Gly Asn Arg
                                                      1

AGC ACC GCG GAC GCG GAC GGG CTG CTG GCT GGG CGC GGG CGG GCC GCG                          163
Ser Thr Ala Asp Ala Asp Gly Leu Leu Ala Gly Arg Gly Arg Ala Ala
  5                  10                  15                  20

GGG GCA TCT GCG GGG GCA TCT GCG GGG CTG GCT GGG CAG GGC GCG GCG                          211
Gly Ala Ser Ala Gly Ala Ser Ala Gly Leu Ala Gly Gln Gly Ala Ala
                 25                  30                  35

GCG CTG GTG GGG GGC GTG CTG CTC ATC GGC GCG GTG CTC GCG GGG AAC                          259
Ala Leu Val Gly Gly Val Leu Leu Ile Gly Ala Val Leu Ala Gly Asn
                 40                  45                  50

TCG CTC GTG TGC GTG AGC GTG GCC ACC GAG CGC GCC CTG CAG ACG CCC                          307
Ser Leu Val Cys Val Ser Val Ala Thr Glu Arg Ala Leu Gln Thr Pro
                 55                  60                  65

ACC AAC TCC TTC ATC GTG AGC CTG GCG GCC GCC GAC CTC CTC CTC GCT                          355
Thr Asn Ser Phe Ile Val Ser Leu Ala Ala Ala Asp Leu Leu Leu Ala
```

|   |   |   |   |   |   |   | 70 |   |   |   |   | 75 |   |   |   |   | 80 |   |   |   |      |
|---|---|---|---|---|---|---|----|---|---|---|---|----|---|---|---|---|----|---|---|---|------|
| CTC | CTG | GTG | CTG | CCG | CTC | TTC | GTC | TAC | TCC | GAG | GTC | CAG | GGT | GGC | GCG | | | | | | 403 |
| Leu | Leu | Val | Leu | Pro | Leu | Phe | Val | Tyr | Ser | Glu | Val | Gln | Gly | Gly | Ala | | | | | | |
| 85 | | | | | 90 | | | | 95 | | | | | | 100 | | | | | | |

| TGG | CTG | CTG | AGC | CCC | CGC | CTG | TGC | GAC | GCC | CTC | ATG | GCC | ATG | GAC | GTC | 451 |
|-----|-----|-----|-----|-----|-----|-----|-----|-----|-----|-----|-----|-----|-----|-----|-----|-----|
| Trp | Leu | Leu | Ser | Pro | Arg | Leu | Cys | Asp | Ala | Leu | Met | Ala | Met | Asp | Val | |
| | | | | 105 | | | | 110 | | | | | 115 | | | |

| ATG | CTG | TGC | ACC | GCC | TCC | ATC | TTC | AAC | CTG | TGC | GCC | ATC | AGC | GTG | GAC | 499 |
| Met | Leu | Cys | Thr | Ala | Ser | Ile | Phe | Asn | Leu | Cys | Ala | Ile | Ser | Val | Asp | |
| | | | 120 | | | | 125 | | | | | 130 | | | | |

| AGG | TTC | GTG | GCC | GTG | GCC | GTG | CCG | CTG | CGC | TAC | AAC | CGG | CAG | GGT | GGG | 547 |
| Arg | Phe | Val | Ala | Val | Ala | Val | Pro | Leu | Arg | Tyr | Asn | Arg | Gln | Gly | Gly | |
| | | 135 | | | | | 140 | | | | | 145 | | | | |

| AGC | CGC | CGG | CAG | CTG | CTG | CTC | ATC | GGC | GCC | ACG | TGG | CTG | CTG | TCC | GCG | 595 |
| Ser | Arg | Arg | Gln | Leu | Leu | Leu | Ile | Gly | Ala | Thr | Trp | Leu | Leu | Ser | Ala | |
| | | 150 | | | | 155 | | | | | 160 | | | | | |

| GCG | GTG | GCG | GCG | CCC | GTA | CTG | TGC | GGC | CTC | AAC | GAC | GTG | CGC | GGC | CGC | 643 |
| Ala | Val | Ala | Ala | Pro | Val | Leu | Cys | Gly | Leu | Asn | Asp | Val | Arg | Gly | Arg | |
| 165 | | | | | 170 | | | | 175 | | | | | | 180 | |

| GAC | CCC | GCC | GTG | TGC | CGC | CTG | GAG | GAC | CGC | GAC | TAC | GTG | GTC | TAC | TCG | 691 |
| Asp | Pro | Ala | Val | Cys | Arg | Leu | Glu | Asp | Arg | Asp | Tyr | Val | Val | Tyr | Ser | |
| | | | | 185 | | | | | 190 | | | | | 195 | | |

| TCC | GTG | TGC | TCC | TTC | TTC | CTA | CCC | TGC | CCG | CTC | ATG | CTG | CTG | CTG | TAC | 739 |
| Ser | Val | Cys | Ser | Phe | Phe | Leu | Pro | Cys | Pro | Leu | Met | Leu | Leu | Leu | Tyr | |
| | | | 200 | | | | | 205 | | | | | | 210 | | |

| TGG | GCC | ACG | TTC | CGC | GGC | CTG | CAG | CGC | TGG | GAG | GTG | GCA | CGT | CGC | GCC | 787 |
| Trp | Ala | Thr | Phe | Arg | Gly | Leu | Gln | Arg | Trp | Glu | Val | Ala | Arg | Arg | Ala | |
| | | 215 | | | | | 220 | | | | | 225 | | | | |

| AAG | CTG | CAC | GGC | CGC | GCG | CCC | CGC | CGA | CCC | AGC | GGC | CCT | GGC | CCG | CCT | 835 |
| Lys | Leu | His | Gly | Arg | Ala | Pro | Arg | Arg | Pro | Ser | Gly | Pro | Gly | Pro | Pro | |
| | 230 | | | | | 235 | | | | | 240 | | | | | |

| TCC | CCC | ACG | CCA | CCC | GCG | CCC | CGC | CTC | CCC | CAG | GAC | CCC | TGC | GGC | CCC | 883 |
| Ser | Pro | Thr | Pro | Pro | Ala | Pro | Arg | Leu | Pro | Gln | Asp | Pro | Cys | Gly | Pro | |
| 245 | | | | | 250 | | | | | 255 | | | | | 260 | |

| GAC | TGT | GCG | CCC | CCC | GCG | CCC | GGC | CTC | CCC | CCG | GAC | CCC | TGC | GGC | TCC | 931 |
| Asp | Cys | Ala | Pro | Pro | Ala | Pro | Gly | Leu | Pro | Pro | Asp | Pro | Cys | Gly | Ser | |
| | | | | 265 | | | | | 270 | | | | | | 275 | |

| AAC | TGT | GCT | CCC | CCC | GAC | GCC | GTC | AGA | GCC | GCC | GCG | CTC | CCA | CCC | CAG | 979 |
| Asn | Cys | Ala | Pro | Pro | Asp | Ala | Val | Arg | Ala | Ala | Ala | Leu | Pro | Pro | Gln | |
| | | | | 280 | | | | | 285 | | | | | 290 | | |

| ACT | CCA | CCG | CAG | ACC | CGC | AGG | AGG | CGG | CGT | GCC | AAG | ATC | ACC | GGC | CGG | 1027 |
| Thr | Pro | Pro | Gln | Thr | Arg | Arg | Arg | Arg | Arg | Ala | Lys | Ile | Thr | Gly | Arg | |
| | | 295 | | | | | 300 | | | | | 305 | | | | |

| GAG | CGC | AAG | GCC | ATG | AGG | GTC | CTG | CCG | GTG | GTG | GTC | GGG | GCC | TTC | CTG | 1075 |
| Glu | Arg | Lys | Ala | Met | Arg | Val | Leu | Pro | Val | Val | Val | Gly | Ala | Phe | Leu | |
| | 310 | | | | | 315 | | | | | 320 | | | | | |

| CTG | TGC | TGG | ACG | CCC | TTC | TTC | GTG | GTG | CAC | ATC | ACG | CAG | GCG | CTG | TGT | 1123 |
| Leu | Cys | Trp | Thr | Pro | Phe | Phe | Val | Val | His | Ile | Thr | Gln | Ala | Leu | Cys | |
| 325 | | | | | 330 | | | | | 335 | | | | | 340 | |

| CCT | GCC | TGC | TCC | GTG | CCC | CCG | CGG | CTG | GTC | AGC | GCC | GTC | ACC | TGG | CTG | 1171 |
| Pro | Ala | Cys | Ser | Val | Pro | Pro | Arg | Leu | Val | Ser | Ala | Val | Thr | Trp | Leu | |
| | | | | 345 | | | | | 350 | | | | | 355 | | |

| GGC | TAC | GTC | AAC | AGC | GCC | CTC | ACC | CCC | GTC | ATC | TAC | ACT | GTC | TTC | AAC | 1219 |
| Gly | Tyr | Val | Asn | Ser | Ala | Leu | Thr | Pro | Val | Ile | Tyr | Thr | Val | Phe | Asn | |
| | | | 360 | | | | | 365 | | | | | 370 | | | |

| GCC | GAG | TTC | CGC | AAC | GTC | TTC | CGC | AAG | GCC | CTG | CGT | GCC | TGC | TGC | TGAGCCGG | 1274 |
| Ala | Glu | Phe | Arg | Asn | Val | Phe | Arg | Lys | Ala | Leu | Arg | Ala | Cys | Cys | | |
| | | 375 | | | | | 380 | | | | | 385 | | | | |

ACCCCCGGAC GCCCCCCGGC CTGATGGCCA GGCCTCAGGG ACCAAGGAGA TGGGGAGGGC  1334

GCTTTTGTAC GTTAATTAAA CAAATTCCTT CCCAAA                                          1370

( 2 ) INFORMATION FOR SEQ ID NO:2:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Asn Arg Ser Thr Ala Asp Ala Asp Gly Leu Leu Ala Gly Arg
 1           5                   10                  15

Gly Arg Ala Ala Gly Ala Ser Ala Gly Ala Ser Ala Gly Leu Ala Gly
            20                  25                  30

Gln Gly Ala Ala Ala Leu Val Gly Val Leu Leu Ile Gly Ala Val
            35                  40                  45

Leu Ala Gly Asn Ser Leu Val Cys Val Ser Val Ala Thr Glu Arg Ala
     50                  55                  60

Leu Gln Thr Pro Thr Asn Ser Phe Ile Val Ser Leu Ala Ala Ala Asp
 65                  70                  75                  80

Leu Leu Leu Ala Leu Leu Val Leu Pro Leu Phe Val Tyr Ser Glu Val
                 85                  90                  95

Gln Gly Gly Ala Trp Leu Leu Ser Pro Arg Leu Cys Asp Ala Leu Met
            100                 105                 110

Ala Met Asp Val Met Leu Cys Thr Ala Ser Ile Phe Asn Leu Cys Ala
            115                 120                 125

Ile Ser Val Asp Arg Phe Val Ala Val Ala Val Pro Leu Arg Tyr Asn
     130                 135                 140

Arg Gln Gly Gly Ser Arg Arg Gln Leu Leu Leu Ile Gly Ala Thr Trp
145                 150                 155                 160

Leu Leu Ser Ala Ala Val Ala Ala Pro Val Leu Cys Gly Leu Asn Asp
                165                 170                 175

Val Arg Gly Arg Asp Pro Ala Val Cys Arg Leu Glu Asp Arg Asp Tyr
            180                 185                 190

Val Val Tyr Ser Ser Val Cys Ser Phe Phe Leu Pro Cys Pro Leu Met
        195                 200                 205

Leu Leu Leu Tyr Trp Ala Thr Phe Arg Gly Leu Gln Arg Trp Glu Val
    210                 215                 220

Ala Arg Arg Ala Lys Leu His Gly Arg Ala Pro Arg Arg Pro Ser Gly
225                 230                 235                 240

Pro Gly Pro Pro Ser Pro Thr Pro Pro Ala Pro Arg Leu Pro Gln Asp
                245                 250                 255

Pro Cys Gly Pro Asp Cys Ala Pro Pro Ala Pro Gly Leu Pro Pro Asp
            260                 265                 270

Pro Cys Gly Ser Asn Cys Ala Pro Pro Asp Ala Val Arg Ala Ala Ala
            275                 280                 285

Leu Pro Pro Gln Thr Pro Pro Gln Thr Arg Arg Arg Arg Arg Ala Lys
    290                 295                 300

Ile Thr Gly Arg Glu Arg Lys Ala Met Arg Val Leu Pro Val Val Val
305                 310                 315                 320

Gly Ala Phe Leu Leu Cys Trp Thr Pro Phe Phe Val Val His Ile Thr
                325                 330                 335

Gln Ala Leu Cys Pro Ala Cys Ser Val Pro Pro Arg Leu Val Ser Ala
            340                 345                 350
```

| Val | Thr | Trp | Leu | Gly | Tyr | Val | Asn | Ser | Ala | Leu | Thr | Pro | Val | Ile | Tyr |
|---|---|---|---|---|---|---|---|---|---|---|---|---|---|---|---|
| | | 355 | | | | | 360 | | | | | 365 | | | |

| Thr | Val | Phe | Asn | Ala | Glu | Phe | Arg | Asn | Val | Phe | Arg | Lys | Ala | Leu | Arg |
|---|---|---|---|---|---|---|---|---|---|---|---|---|---|---|---|
| 370 | | | | | | 375 | | | | | 380 | | | | |

| Ala | Cys | Cys |
|---|---|---|
| 385 | | |

( 2 ) INFORMATION FOR SEQ ID NO:3:

( i ) SEQUENCE CHARACTERISTICS:
        ( A ) LENGTH: 1466 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..103

( i x ) FEATURE:
        ( A ) NAME/KEY: 3'UTR
        ( B ) LOCATION: 1364..1466

( i x ) FEATURE:
        ( A ) NAME/KEY: CDS
        ( B ) LOCATION: 104..1363

( x i ) SEQUENCE DESCRIPTION: SEQ ID NO:3:

| CGGGGGCGGG | ACCAGGGTCC | GGCCGGGGCG | TGCCCCCGGG | GAGGGACTCC | CCGGCTTGCC | 60 |
|---|---|---|---|---|---|---|

| CCCCGGCGTT | GTCCGCGGTG | CTCAGCGCCC | GCCCGGGCGC | GCC | ATG | GGG | AAC | CGC | 115 |
|---|---|---|---|---|---|---|---|---|---|
| | | | | | Met | Gly | Asn | Arg | |
| | | | | | 1 | | | | |

| AGC | ACC | GCG | GAC | GCG | GAC | GGG | CTG | CTG | GCT | GGG | CGC | GGG | CGG | GCC | GCG | 163 |
|---|---|---|---|---|---|---|---|---|---|---|---|---|---|---|---|---|
| Ser | Thr | Ala | Asp | Ala | Asp | Gly | Leu | Leu | Ala | Gly | Arg | Gly | Arg | Ala | Ala | |
| 5 | | | | 10 | | | | | 15 | | | | | 20 | | |

| GGG | GCA | TCT | GCG | GGG | GCA | TCT | GCG | GGG | CTG | GCT | GGG | CAG | GGC | GCG | GCG | 211 |
|---|---|---|---|---|---|---|---|---|---|---|---|---|---|---|---|---|
| Gly | Ala | Ser | Ala | Gly | Ala | Ser | Ala | Gly | Leu | Ala | Gly | Gln | Gly | Ala | Ala | |
| | | | 25 | | | | 30 | | | | | 35 | | | | |

| GCG | CTG | GTG | GGG | GGC | GTG | CTG | CTC | ATC | GGC | GCG | GTG | CTC | GCG | GGG | AAC | 259 |
|---|---|---|---|---|---|---|---|---|---|---|---|---|---|---|---|---|
| Ala | Leu | Val | Gly | Gly | Val | Leu | Leu | Ile | Gly | Ala | Val | Leu | Ala | Gly | Asn | |
| | | | 40 | | | | | 45 | | | | | 50 | | | |

| TCG | CTC | GTG | TGC | GTG | AGC | GTG | GCC | ACC | GAG | CGC | GCC | CTG | CAG | ACG | CCC | 307 |
|---|---|---|---|---|---|---|---|---|---|---|---|---|---|---|---|---|
| Ser | Leu | Val | Cys | Val | Ser | Val | Ala | Thr | Glu | Arg | Ala | Leu | Gln | Thr | Pro | |
| | | 55 | | | | | 60 | | | | | 65 | | | | |

| ACC | AAC | TCC | TTC | ATC | GTG | AGC | CTG | GCG | GCC | GCC | GAC | CTC | CTC | CTC | GCT | 355 |
|---|---|---|---|---|---|---|---|---|---|---|---|---|---|---|---|---|
| Thr | Asn | Ser | Phe | Ile | Val | Ser | Leu | Ala | Ala | Ala | Asp | Leu | Leu | Leu | Ala | |
| | 70 | | | | | 75 | | | | | 80 | | | | | |

| CTC | CTG | GTG | CTG | CCG | CTC | TTC | GTC | TAC | TCC | GAG | GTC | CAG | GGT | GGC | GCG | 403 |
|---|---|---|---|---|---|---|---|---|---|---|---|---|---|---|---|---|
| Leu | Leu | Val | Leu | Pro | Leu | Phe | Val | Tyr | Ser | Glu | Val | Gln | Gly | Gly | Ala | |
| 85 | | | | | 90 | | | | | 95 | | | | | 100 | |

| TGG | CTG | CTG | AGC | CCC | CGC | CTG | TGC | GAC | GCC | CTC | ATG | GCC | ATG | GAC | GTC | 451 |
|---|---|---|---|---|---|---|---|---|---|---|---|---|---|---|---|---|
| Trp | Leu | Leu | Ser | Pro | Arg | Leu | Cys | Asp | Ala | Leu | Met | Ala | Met | Asp | Val | |
| | | | | 105 | | | | | 110 | | | | | 115 | | |

| ATG | CTG | TGC | ACC | GCC | TCC | ATC | TTC | AAC | CTG | TGC | GCC | ATC | AGC | GTG | GAC | 499 |
|---|---|---|---|---|---|---|---|---|---|---|---|---|---|---|---|---|
| Met | Leu | Cys | Thr | Ala | Ser | Ile | Phe | Asn | Leu | Cys | Ala | Ile | Ser | Val | Asp | |
| | | | 120 | | | | | 125 | | | | | 130 | | | |

| AGG | TTC | GTG | GCC | GTG | GCC | GTG | CCG | CTG | CGC | TAC | AAC | CGG | CAG | GGT | GGG | 547 |
|---|---|---|---|---|---|---|---|---|---|---|---|---|---|---|---|---|
| Arg | Phe | Val | Ala | Val | Ala | Val | Pro | Leu | Arg | Tyr | Asn | Arg | Gln | Gly | Gly | |
| | | | 135 | | | | | 140 | | | | | 145 | | | |

| AGC | CGC | CGG | CAG | CTG | CTG | CTC | ATC | GGC | GCC | ACG | TGG | CTG | CTG | TCC | GCG | 595 |
|---|---|---|---|---|---|---|---|---|---|---|---|---|---|---|---|---|
| Ser | Arg | Arg | Gln | Leu | Leu | Leu | Ile | Gly | Ala | Thr | Trp | Leu | Leu | Ser | Ala | |
| | 150 | | | | | 155 | | | | | 160 | | | | | |

| | | | | | | | | | | | | | | | | |
|---|---|---|---|---|---|---|---|---|---|---|---|---|---|---|---|---|
| GCG | GTG | GCG | GCG | CCC | GTA | CTG | TGC | GGC | CTC | AAC | GAC | GTG | CGC | GGC | CGC | 643 |
| Ala | Val | Ala | Ala | Pro | Val | Leu | Cys | Gly | Leu | Asn | Asp | Val | Arg | Gly | Arg | |
| 165 | | | | 170 | | | | | 175 | | | | | 180 | | |
| GAC | CCC | GCC | GTG | TGC | CGC | CTG | GAG | GAC | CGC | GAC | TAC | GTG | GTC | TAC | TCG | 691 |
| Asp | Pro | Ala | Val | Cys | Arg | Leu | Glu | Asp | Arg | Asp | Tyr | Val | Val | Tyr | Ser | |
| | | | | 185 | | | | | 190 | | | | | 195 | | |
| TCC | GTG | TGC | TCC | TTC | TTC | CTA | CCC | TGC | CCG | CTC | ATG | CTG | CTG | CTG | TAC | 739 |
| Ser | Val | Cys | Ser | Phe | Phe | Leu | Pro | Cys | Pro | Leu | Met | Leu | Leu | Leu | Tyr | |
| | | | 200 | | | | | 205 | | | | | 210 | | | |
| TGG | GCC | ACG | TTC | CGC | GGC | CTG | CAG | CGC | TGG | GAG | GTG | GCA | CGT | CGC | GCC | 787 |
| Trp | Ala | Thr | Phe | Arg | Gly | Leu | Gln | Arg | Trp | Glu | Val | Ala | Arg | Arg | Ala | |
| | | 215 | | | | | 220 | | | | | 225 | | | | |
| AAG | CTG | CAC | GGC | CGC | GCG | CCC | CGC | CGA | CCC | AGC | GGC | CCT | GGC | CCG | CCT | 835 |
| Lys | Leu | His | Gly | Arg | Ala | Pro | Arg | Arg | Pro | Ser | Gly | Pro | Gly | Pro | Pro | |
| | 230 | | | | 235 | | | | | 240 | | | | | | |
| TCC | CCC | ACG | CCA | CCC | GCG | CCC | CGC | CTC | CCC | CAG | GAC | CCC | TGC | GGC | CCC | 883 |
| Ser | Pro | Thr | Pro | Pro | Ala | Pro | Arg | Leu | Pro | Gln | Asp | Pro | Cys | Gly | Pro | |
| 245 | | | | 250 | | | | | 255 | | | | | 260 | | |
| GAC | TGT | GCG | CCC | CCC | GCG | CCC | GGC | CTT | CCC | CGG | GGT | CCC | TGC | GGC | CCC | 931 |
| Asp | Cys | Ala | Pro | Pro | Ala | Pro | Gly | Leu | Pro | Arg | Gly | Pro | Cys | Gly | Pro | |
| | | | | 265 | | | | | 270 | | | | | 275 | | |
| GAC | TGT | GCG | CCC | GCC | GCG | CCC | AGC | CTC | CCC | CAG | GAC | CCC | TGC | GGC | CCC | 979 |
| Asp | Cys | Ala | Pro | Ala | Ala | Pro | Ser | Leu | Pro | Gln | Asp | Pro | Cys | Gly | Pro | |
| | | | 280 | | | | | 285 | | | | | 290 | | | |
| GAC | TGT | GCG | CCC | CCC | GCG | CCC | GGC | CTC | CCC | CCG | GAC | CCC | TGC | GGC | TCC | 1027 |
| Asp | Cys | Ala | Pro | Pro | Ala | Pro | Gly | Leu | Pro | Pro | Asp | Pro | Cys | Gly | Ser | |
| | | 295 | | | | | 300 | | | | | 305 | | | | |
| AAC | TGT | GCT | CCC | CCC | GAC | GCC | GTC | AGA | GCC | GCC | GCG | CTC | CCA | CCC | CAG | 1075 |
| Asn | Cys | Ala | Pro | Pro | Asp | Ala | Val | Arg | Ala | Ala | Ala | Leu | Pro | Pro | Gln | |
| 310 | | | | | 315 | | | | | 320 | | | | | | |
| ACT | CCA | CCG | CAG | ACC | CGC | AGG | AGG | CGG | CGT | GCC | AAG | ATC | ACC | GGC | CGG | 1123 |
| Thr | Pro | Pro | Gln | Thr | Arg | Arg | Arg | Arg | Arg | Ala | Lys | Ile | Thr | Gly | Arg | |
| 325 | | | | | 330 | | | | | 335 | | | | | 340 | |
| GAG | CGC | AAG | GCC | ATG | AGG | GTC | CTG | CCG | GTG | GTG | GTC | GGG | GCC | TTC | CTG | 1171 |
| Glu | Arg | Lys | Ala | Met | Arg | Val | Leu | Pro | Val | Val | Val | Gly | Ala | Phe | Leu | |
| | | | | 345 | | | | | 350 | | | | | 355 | | |
| CTG | TGC | TGG | ACG | CCC | TTC | TTC | GTG | GTG | CAC | ATC | ACG | CAG | GCG | CTG | TGT | 1219 |
| Leu | Cys | Trp | Thr | Pro | Phe | Phe | Val | Val | His | Ile | Thr | Gln | Ala | Leu | Cys | |
| | | | 360 | | | | | 365 | | | | | 370 | | | |
| CCT | GCC | TGC | TCC | GTG | CCC | CCG | CGG | CTG | GTC | AGC | GCC | GTC | ACC | TGG | CTG | 1267 |
| Pro | Ala | Cys | Ser | Val | Pro | Pro | Arg | Leu | Val | Ser | Ala | Val | Thr | Trp | Leu | |
| | | 375 | | | | | 380 | | | | | 385 | | | | |
| GGC | TAC | GTC | AAC | AGC | GCC | CTC | ACC | CCC | GTC | ATC | TAC | ACT | GTC | TTC | AAC | 1315 |
| Gly | Tyr | Val | Asn | Ser | Ala | Leu | Thr | Pro | Val | Ile | Tyr | Thr | Val | Phe | Asn | |
| | 390 | | | | | 395 | | | | | 400 | | | | | |
| GCC | GAG | TTC | CGC | AAC | GTC | TTC | CGC | AAG | GCC | CTG | CGT | GCC | TGC | TGC | TGAGCCGG | 1370 |
| Ala | Glu | Phe | Arg | Asn | Val | Phe | Arg | Lys | Ala | Leu | Arg | Ala | Cys | Cys | | |
| 405 | | | | | 410 | | | | | 415 | | | | 420 | | |

ACCCCGGAC GCCCCCGGC CTGATGGCCA GGCCTCAGGG ACCAAGGAGA TGGGGAGGGC        1430

GCTTTTGTAC GTTAATTAAA CAAATTCCTT CCCAAA        1466

( 2 ) INFORMATION FOR SEQ ID NO:4:

( i ) SEQUENCE CHARACTERISTICS:
    ( A ) LENGTH: 419 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

| Met<br>1 | Gly | Asn | Arg | Ser<br>5 | Thr | Ala | Asp | Ala | Asp<br>10 | Gly | Leu | Leu | Ala | Gly<br>15 | Arg |
|---|---|---|---|---|---|---|---|---|---|---|---|---|---|---|---|
| Gly | Arg | Ala | Ala<br>20 | Gly | Ala | Ser | Ala | Gly<br>25 | Ala | Ser | Ala | Gly | Leu<br>30 | Ala | Gly |
| Gln | Gly | Ala<br>35 | Ala | Ala | Leu | Val | Gly<br>40 | Gly | Val | Leu | Leu | Ile<br>45 | Gly | Ala | Val |
| Leu | Ala<br>50 | Gly | Asn | Ser | Leu | Val<br>55 | Cys | Val | Ser | Val | Ala<br>60 | Thr | Glu | Arg | Ala |
| Leu<br>65 | Gln | Thr | Pro | Thr | Asn<br>70 | Ser | Phe | Ile | Val | Ser<br>75 | Leu | Ala | Ala | Ala | Asp<br>80 |
| Leu | Leu | Leu | Ala | Leu<br>85 | Leu | Val | Leu | Pro | Leu<br>90 | Phe | Val | Tyr | Ser | Glu<br>95 | Val |
| Gln | Gly | Gly | Ala<br>100 | Trp | Leu | Leu | Ser | Pro<br>105 | Arg | Leu | Cys | Asp | Ala<br>110 | Leu | Met |
| Ala | Met | Asp<br>115 | Val | Met | Leu | Cys | Thr<br>120 | Ala | Ser | Ile | Phe | Asn<br>125 | Leu | Cys | Ala |
| Ile | Ser | Val<br>130 | Asp | Arg | Phe | Val<br>135 | Ala | Val | Ala | Val | Pro<br>140 | Leu | Arg | Tyr | Asn |
| Arg<br>145 | Gln | Gly | Gly | Ser | Arg<br>150 | Arg | Gln | Leu | Leu | Leu<br>155 | Ile | Gly | Ala | Thr | Trp<br>160 |
| Leu | Leu | Ser | Ala | Ala<br>165 | Val | Ala | Ala | Pro | Val<br>170 | Leu | Cys | Gly | Leu | Asn<br>175 | Asp |
| Val | Arg | Gly | Arg<br>180 | Asp | Pro | Ala | Val | Cys<br>185 | Arg | Leu | Glu | Asp | Arg<br>190 | Asp | Tyr |
| Val | Val | Tyr<br>195 | Ser | Ser | Val | Cys<br>200 | Ser | Phe | Phe | Leu | Pro<br>205 | Cys | Pro | Leu | Met |
| Leu | Leu<br>210 | Leu | Tyr | Trp | Ala | Thr<br>215 | Phe | Arg | Gly | Leu | Gln<br>220 | Arg | Trp | Glu | Val |
| Ala<br>225 | Arg | Arg | Ala | Lys | Leu<br>230 | His | Gly | Arg | Ala | Pro<br>235 | Arg | Arg | Pro | Ser | Gly<br>240 |
| Pro | Gly | Pro | Pro | Ser<br>245 | Pro | Thr | Pro | Pro | Ala<br>250 | Pro | Arg | Leu | Pro | Gln<br>255 | Asp |
| Pro | Cys | Gly<br>260 | Pro | Asp | Cys | Ala | Pro<br>265 | Pro | Ala | Pro | Gly | Leu<br>270 | Pro | Arg | Gly |
| Pro | Cys<br>275 | Gly | Pro | Asp | Cys | Ala<br>280 | Pro | Ala | Ala | Pro | Ser<br>285 | Leu | Pro | Gln | Asp |
| Pro | Cys<br>290 | Gly | Pro | Asp | Cys | Ala<br>295 | Pro | Pro | Ala | Pro | Gly<br>300 | Leu | Pro | Pro | Asp |
| Pro<br>305 | Cys | Gly | Ser | Asn | Cys<br>310 | Ala | Pro | Pro | Asp<br>315 | Ala | Val | Arg | Ala | Ala | Ala<br>320 |
| Leu | Pro | Pro | Gln | Thr<br>325 | Pro | Pro | Gln | Thr | Arg<br>330 | Arg | Arg | Arg | Arg | Ala<br>335 | Lys |
| Ile | Thr | Gly | Arg<br>340 | Glu | Arg | Lys | Ala | Met<br>345 | Arg | Val | Leu | Pro | Val<br>350 | Val | Val |
| Gly | Ala | Phe<br>355 | Leu | Leu | Cys | Trp | Thr<br>360 | Pro | Phe | Phe | Val | Val<br>365 | His | Ile | Thr |
| Gln | Ala<br>370 | Leu | Cys | Pro | Ala | Cys<br>375 | Ser | Val | Pro | Pro | Arg<br>380 | Leu | Val | Ser | Ala |
| Val<br>385 | Thr | Trp | Leu | Gly | Tyr<br>390 | Val | Asn | Ser | Ala | Leu<br>395 | Thr | Pro | Val | Ile | Tyr<br>400 |
| Thr | Val | Phe | Asn | Ala<br>405 | Glu | Phe | Arg | Asn | Val<br>410 | Phe | Arg | Lys | Ala | Leu<br>415 | Arg |
| Ala | Cys | Cys | | | | | | | | | | | | | |

( 2 ) INFORMATION FOR SEQ ID NO:5:

( i ) SEQUENCE CHARACTERISTICS:
        ( A ) LENGTH: 1610 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..103

( i x ) FEATURE:
        ( A ) NAME/KEY: 3'UTR
        ( B ) LOCATION: 1508..1610

( i x ) FEATURE:
        ( A ) NAME/KEY: CDS
        ( B ) LOCATION: 104..1507

( x i ) SEQUENCE DESCRIPTION: SEQ ID NO:5:

```
CGGGGGCGGG ACCAGGGTCC GGCCGGGGCG TGCCCCCGGG GAGGGACTCC CCGGCTTGCC                 60

CCCCGGCGTT GTCCGCGGTG CTCAGCGCCC GCCCGGGCGC GCC ATG GGG AAC CGC                 115
                                              Met Gly Asn Arg
                                               1

AGC ACC GCG GAC GCG GAC GGG CTG CTG GCT GGG CGC GGG CGG GCC GCG                 163
Ser Thr Ala Asp Ala Asp Gly Leu Leu Ala Gly Arg Gly Arg Ala Ala
 5              10                  15                  20

GGG GCA TCT GCG GGG GCA TCT GCG GGG CTG GCT GGG CAG GGC GCG GCG                 211
Gly Ala Ser Ala Gly Ala Ser Ala Gly Leu Ala Gly Gln Gly Ala Ala
                 25                  30                  35

GCG CTG GTG GGG GGC GTG CTG CTC ATC GGC GCG GTG CTC GCG GGG AAC                 259
Ala Leu Val Gly Gly Val Leu Leu Ile Gly Ala Val Leu Ala Gly Asn
             40                  45                  50

TCG CTC GTG TGC GTG AGC GTG GCC ACC GAG CGC GCC CTG CAG ACG CCC                 307
Ser Leu Val Cys Val Ser Val Ala Thr Glu Arg Ala Leu Gln Thr Pro
         55                  60                  65

ACC AAC TCC TTC ATC GTG AGC CTG GCG GCC GCC GAC CTC CTC CTC GCT                 355
Thr Asn Ser Phe Ile Val Ser Leu Ala Ala Ala Asp Leu Leu Leu Ala
     70                  75                  80

CTC CTG GTG CTG CCG CTC TTC GTC TAC TCC GAG GTC CAG GGT GGC GCG                 403
Leu Leu Val Leu Pro Leu Phe Val Tyr Ser Glu Val Gln Gly Gly Ala
 85                  90                  95                 100

TGG CTG CTG AGC CCC CGC CTG TGC GAC GCC CTC ATG GCC ATG GAC GTC                 451
Trp Leu Leu Ser Pro Arg Leu Cys Asp Ala Leu Met Ala Met Asp Val
                105                 110                 115

ATG CTG TGC ACC GCC TCC ATC TTC AAC CTG TGC GCC ATC AGC GTG GAC                 499
Met Leu Cys Thr Ala Ser Ile Phe Asn Leu Cys Ala Ile Ser Val Asp
            120                 125                 130

AGG TTC GTG GCC GTG GCC GTG CCG CTG CGC TAC AAC CGG CAG GGT GGG                 547
Arg Phe Val Ala Val Ala Val Pro Leu Arg Tyr Asn Arg Gln Gly Gly
        135                 140                 145

AGC CGC CGG CAG CTG CTG CTC ATC GGC GCC ACG TGG CTG CTG TCC GCG                 595
Ser Arg Arg Gln Leu Leu Leu Ile Gly Ala Thr Trp Leu Leu Ser Ala
    150                 155                 160

GCG GTG GCG GCG CCC GTA CTG TGC GGC CTC AAC GAC GTG CGC GGC CGC                 643
Ala Val Ala Ala Pro Val Leu Cys Gly Leu Asn Asp Val Arg Gly Arg
165                 170                 175                 180

GAC CCC GCC GTG TGC CGC CTG GAG GAC CGC GAC TAC GTG GTC TAC TCG                 691
Asp Pro Ala Val Cys Arg Leu Glu Asp Arg Asp Tyr Val Val Tyr Ser
                185                 190                 195

TCC GTG TGC TCC TTC TTC CTA CCC TGC CCG CTC ATG CTG CTG CTG TAC                 739
```

| | | | | | | | | | | | | | | | | |
|---|---|---|---|---|---|---|---|---|---|---|---|---|---|---|---|---|
| Ser | Val | Cys | Ser 200 | Phe | Phe | Leu | Pro | Cys 205 | Pro | Leu | Met | Leu | Leu 210 | Leu | Tyr | |
| TGG | GCC | ACG | TTC | CGC | GGC | CTG | CAG | CGC | TGG | GAG | GTG | GCA | CGT | CGC | GCC | 787 |
| Trp | Ala | Thr 215 | Phe | Arg | Gly | Leu | Gln 220 | Arg | Trp | Glu | Val | Ala 225 | Arg | Arg | Ala | |
| AAG | CTG | CAC | GGC | CGC | GCG | CCC | CGC | CGA | CCC | AGC | GGC | CCT | GGC | CCG | CCT | 835 |
| Lys | Leu | His 230 | Gly | Arg | Ala | Pro | Arg 235 | Arg | Pro | Ser | Gly | Pro 240 | Gly | Pro | Pro | |
| TCC | CCC | ACG | CCA | CCC | GCG | CCC | CGC | CTC | CCC | CAG | GAC | CCC | TGC | GGC | CCC | 883 |
| Ser 245 | Pro | Thr | Pro | Pro | Ala 250 | Pro | Arg | Leu | Pro | Gln 255 | Asp | Pro | Cys | Gly | Pro 260 | |
| GAC | TGT | GCG | CCC | CCC | GCG | CCC | GGC | CTT | CCC | CGG | GGT | CCC | TGC | GGC | CCC | 931 |
| Asp | Cys | Ala | Pro 265 | Pro | Ala | Pro | Gly | Leu | Pro 270 | Arg | Gly | Pro | Cys | Gly 275 | Pro | |
| GAC | TGT | GCG | CCC | GCC | GCG | CCC | GGC | CTC | CCC | CCG | GAC | CCC | TGC | GGC | CCC | 979 |
| Asp | Cys | Ala | Pro 280 | Ala | Ala | Pro | Gly | Leu | Pro 285 | Pro | Asp | Pro | Cys | Gly 290 | Pro | |
| GAC | TGT | GCG | CCC | CCC | GCG | CCC | GGC | CTC | CCC | CAG | GAC | CCC | TGC | GGC | CCC | 1027 |
| Asp | Cys | Ala | Pro 295 | Pro | Ala | Pro | Gly | Leu 300 | Pro | Gln | Asp | Pro | Cys 305 | Gly | Pro | |
| GAC | TGT | GCG | CCC | CCC | GCG | CCC | GGC | CTT | CCC | CGG | GGT | CCC | TGC | GGC | CCC | 1075 |
| Asp | Cys | Ala 310 | Pro | Pro | Ala | Pro | Gly 315 | Leu | Pro | Arg | Gly 320 | Pro | Cys | Gly | Pro | |
| GAC | TGT | GCG | CCC | CCC | GCG | CCC | GGC | CTC | CCC | CAG | GAC | CCC | TGC | GGC | CCC | 1123 |
| Asp 325 | Cys | Ala | Pro | Pro | Ala 330 | Pro | Gly | Leu | Pro | Gln 335 | Asp | Pro | Cys | Gly | Pro 340 | |
| GAC | TGT | GCG | CCC | CCC | GCG | CCC | GGC | CTC | CCC | CCG | GAC | CCC | TGC | GGC | TCC | 1171 |
| Asp | Cys | Ala | Pro | Pro 345 | Ala | Pro | Gly | Leu | Pro 350 | Pro | Asp | Pro | Cys | Gly 355 | Ser | |
| AAC | TGT | GCT | CCC | CCC | GAC | GCC | GTC | AGA | GCC | GCC | GCG | CTC | CCA | CCC | CAG | 1219 |
| Asn | Cys | Ala | Pro 360 | Pro | Asp | Ala | Val | Arg 365 | Ala | Ala | Ala | Leu | Pro 370 | Pro | Gln | |
| ACT | CCA | CCG | CAG | ACC | CGC | AGG | AGG | CGG | CGT | GCC | AAG | ATC | ACC | GGC | CGG | 1267 |
| Thr | Pro | Pro 375 | Gln | Thr | Arg | Arg | Arg 380 | Arg | Arg | Ala | Lys | Ile 385 | Thr | Gly | Arg | |
| GAG | CGC | AAG | GCC | ATG | AGG | GTC | CTG | CCG | GTG | GTG | GTC | GGG | GCC | TTC | CTG | 1315 |
| Glu | Arg 390 | Lys | Ala | Met | Arg | Val 395 | Leu | Pro | Val | Val | Val 400 | Gly | Ala | Phe | Leu | |
| CTG | TGC | TGG | ACG | CCC | TTC | TTC | GTG | GTG | CAC | ATC | ACG | CAG | GCG | CTG | TGT | 1363 |
| Leu 405 | Cys | Trp | Thr | Pro | Phe 410 | Phe | Val | Val | His | Ile 415 | Thr | Gln | Ala | Leu | Cys 420 | |
| CCT | GCC | TGC | TCC | GTG | CCC | CCG | CGG | CTG | GTC | AGC | GCC | GTC | ACC | TGG | CTG | 1411 |
| Pro | Ala | Cys | Ser | Val 425 | Pro | Pro | Arg | Leu | Val 430 | Ser | Ala | Val | Thr | Trp 435 | Leu | |
| GGC | TAC | GTC | AAC | AGC | GCC | CTC | ACC | CCC | GTC | ATC | TAC | ACT | GTC | TTC | AAC | 1459 |
| Gly | Tyr | Val | Asn 440 | Ser | Ala | Leu | Thr | Pro | Val 445 | Ile | Tyr | Thr | Val | Phe 450 | Asn | |
| GCC | GAG | TTC | CGC | AAC | GTC | TTC | CGC | AAG | GCC | CTG | CGT | GCC | TGC | TGC | TGAGCCGG | 1514 |
| Ala | Glu | Phe 455 | Arg | Asn | Val | Phe | Arg 460 | Lys | Ala | Leu | Arg | Ala 465 | Cys | Cys | | |
| ACCCCGGAC | GCCCCCGGC | CTGATGGCCA | GGCCTCAGGG | ACCAAGGAGA | TGGGGAGGGC | | | | | | | | | | | 1574 |
| GCTTTTGTAC | GTTAATTAAA | CAAATTCCTT | CCCAAA | | | | | | | | | | | | | 1610 |

( 2 ) INFORMATION FOR SEQ ID NO:6:

( i ) SEQUENCE CHARACTERISTICS:
        ( A ) LENGTH: 467 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Gly | Asn | Arg | Ser | Thr | Ala | Asp | Ala | Asp | Gly | Leu | Leu | Ala | Gly | Arg |
| 1 | | | | 5 | | | | | 10 | | | | | 15 | |
| Gly | Arg | Ala | Ala | Gly | Ala | Ser | Ala | Gly | Ala | Ser | Ala | Gly | Leu | Ala | Gly |
| | | | 20 | | | | | 25 | | | | | 30 | | |
| Gln | Gly | Ala | Ala | Ala | Leu | Val | Gly | Gly | Val | Leu | Leu | Ile | Gly | Ala | Val |
| | | | 35 | | | | | 40 | | | | | 45 | | |
| Leu | Ala | Gly | Asn | Ser | Leu | Val | Cys | Val | Ser | Val | Ala | Thr | Glu | Arg | Ala |
| | 50 | | | | | 55 | | | | | 60 | | | | |
| Leu | Gln | Thr | Pro | Thr | Asn | Ser | Phe | Ile | Val | Ser | Leu | Ala | Ala | Ala | Asp |
| 65 | | | | | 70 | | | | | 75 | | | | | 80 |
| Leu | Leu | Leu | Ala | Leu | Leu | Val | Leu | Pro | Leu | Phe | Val | Tyr | Ser | Glu | Val |
| | | | | 85 | | | | | 90 | | | | | 95 | |
| Gln | Gly | Gly | Ala | Trp | Leu | Leu | Ser | Pro | Arg | Leu | Cys | Asp | Ala | Leu | Met |
| | | | 100 | | | | | 105 | | | | | 110 | | |
| Ala | Met | Asp | Val | Met | Leu | Cys | Thr | Ala | Ser | Ile | Phe | Asn | Leu | Cys | Ala |
| | | 115 | | | | | 120 | | | | | 125 | | | |
| Ile | Ser | Val | Asp | Arg | Phe | Val | Ala | Val | Ala | Val | Pro | Leu | Arg | Tyr | Asn |
| | 130 | | | | | 135 | | | | | 140 | | | | |
| Arg | Gln | Gly | Gly | Ser | Arg | Arg | Gln | Leu | Leu | Leu | Ile | Gly | Ala | Thr | Trp |
| 145 | | | | | 150 | | | | | 155 | | | | | 160 |
| Leu | Leu | Ser | Ala | Ala | Val | Ala | Ala | Pro | Val | Leu | Cys | Gly | Leu | Asn | Asp |
| | | | | 165 | | | | | 170 | | | | | 175 | |
| Val | Arg | Gly | Arg | Asp | Pro | Ala | Val | Cys | Arg | Leu | Glu | Asp | Arg | Asp | Tyr |
| | | | 180 | | | | | 185 | | | | | 190 | | |
| Val | Val | Tyr | Ser | Ser | Val | Cys | Ser | Phe | Phe | Leu | Pro | Cys | Pro | Leu | Met |
| | | 195 | | | | | 200 | | | | | 205 | | | |
| Leu | Leu | Leu | Tyr | Trp | Ala | Thr | Phe | Arg | Gly | Leu | Gln | Arg | Trp | Glu | Val |
| | 210 | | | | | 215 | | | | | 220 | | | | |
| Ala | Arg | Arg | Ala | Lys | Leu | His | Gly | Arg | Ala | Pro | Arg | Arg | Pro | Ser | Gly |
| 225 | | | | | 230 | | | | | 235 | | | | | 240 |
| Pro | Gly | Pro | Pro | Ser | Pro | Thr | Pro | Pro | Ala | Pro | Arg | Leu | Pro | Gln | Asp |
| | | | | 245 | | | | | 250 | | | | | 255 | |
| Pro | Cys | Gly | Pro | Asp | Cys | Ala | Pro | Pro | Ala | Pro | Gly | Leu | Pro | Arg | Gly |
| | | | 260 | | | | | 265 | | | | | 270 | | |
| Pro | Cys | Gly | Pro | Asp | Cys | Ala | Pro | Ala | Ala | Pro | Gly | Leu | Pro | Pro | Asp |
| | | 275 | | | | | 280 | | | | | 285 | | | |
| Pro | Cys | Gly | Pro | Asp | Cys | Ala | Pro | Pro | Ala | Pro | Gly | Leu | Pro | Gln | Asp |
| | 290 | | | | | 295 | | | | | 300 | | | | |
| Pro | Cys | Gly | Pro | Asp | Cys | Ala | Pro | Pro | Ala | Pro | Gly | Leu | Pro | Arg | Gly |
| 305 | | | | | 310 | | | | | 315 | | | | | 320 |
| Pro | Cys | Gly | Pro | Asp | Cys | Ala | Pro | Pro | Ala | Pro | Gly | Leu | Pro | Gln | Asp |
| | | | | 325 | | | | | 330 | | | | | 335 | |
| Pro | Cys | Gly | Pro | Asp | Cys | Ala | Pro | Pro | Ala | Pro | Gly | Leu | Pro | Pro | Asp |
| | | | 340 | | | | | 345 | | | | | 350 | | |
| Pro | Cys | Gly | Ser | Asn | Cys | Ala | Pro | Pro | Asp | Ala | Val | Arg | Ala | Ala | Ala |
| | | 355 | | | | | 360 | | | | | 365 | | | |
| Leu | Pro | Pro | Gln | Thr | Pro | Pro | Gln | Thr | Arg | Arg | Arg | Arg | Arg | Ala | Lys |
| | 370 | | | | | 375 | | | | | 380 | | | | |
| Ile | Thr | Gly | Arg | Glu | Arg | Lys | Ala | Met | Arg | Val | Leu | Pro | Val | Val | Val |
| 385 | | | | | 390 | | | | | 395 | | | | | 400 |
| Gly | Ala | Phe | Leu | Leu | Cys | Trp | Thr | Pro | Phe | Phe | Val | Val | His | Ile | Thr |
| | | | | 405 | | | | | 410 | | | | | 415 | |

| Gln | Ala | Leu | Cys<br>420 | Pro | Ala | Cys | Ser | Val<br>425 | Pro | Pro | Arg | Leu | Val<br>430 | Ser | Ala |
| Val | Thr | Trp<br>435 | Leu | Gly | Tyr | Val | Asn<br>440 | Ser | Ala | Leu | Thr | Pro<br>445 | Val | Ile | Tyr |
| Thr | Val<br>450 | Phe | Asn | Ala | Glu | Phe<br>455 | Arg | Asn | Val | Phe | Arg<br>460 | Lys | Ala | Leu | Arg |
| Ala<br>465 | Cys | Cys | | | | | | | | | | | | | |

What we claim Is:

1. A recombinant expression construct capable of expressing a human dopamine receptor gene in a mammalian host cell, the construct comprising a vaccinia virus vector operably linked to a nucleic acid encoding a human D4 dopamine receptor.

2. The recombinant expression construct of claim 1 comprising a nucleic acid encoding the human D4 dopamine receptor allele D4,2 having an amino acid sequence identified as SEQ ID No.:2.

3. The recombinant expression construct of claim 1 comprising a nucleic acid encoding the human D4 dopamine receptor D4,4 having an amino acid sequence identified as SEQ ID No. :4.

4. The recombinant expression construct of claim 1 comprising a nucleic acid encoding the human D4 dopamine receptor allele D4.7 having an amino acid sequence identified as SEQ ID No.:6.

5. A eukaryotic cell culture transformed with the recombinant expression construct of claim 1.

6. A homogeneous human D4 dopamine receptor protein, made in the eukaryotic cell culture of claim 5.

7. A nucleic acid comprising a vaccinia virus-derived vector that is the vector pZVneo covalently linked to a nucleic acid encoding a human D4 dopamine receptor.

8. The nucleic acid of claim 7 wherein the human D4 dopamine receptor nucleic acid encodes the human D4 dopamine receptor allele D4.2 having an amino acid sequence identified by Sequence I,D. No.: 2.

9. The nucleic acid of claim 7 wherein the human D4 dopamine receptor nucleic acid encodes the human D4 dopamine receptor allele D4.4 having an amino acid sequence identified by Sequence I.D. No,:4.

10. The nucleic acid of claim 7 wherein the human D4 dopamine receptor nucleic acid encodes the human D4dopamine receptor allele D4,7 having an amino acid sequence identified by Sequence I.D. No. :6.

* * * * *